United States Patent [19]
Teuber et al.

[11] Patent Number: 5,922,724
[45] Date of Patent: Jul. 13, 1999

[54] BENZIMIDAZOLE COMPOUNDS AND THEIR USE AS MODULATORS OF THE GABA A RECEPTOR COMPLEX

[75] Inventors: Lene Teuber, Vaerlose; Frank Wätjen, Herlev, both of Denmark; Yoshimasa Fukuda, Yokohama, Japan; Osamu Ushiroda, Yokohama, Japan; Toshiro Sasaki, Yokohama, Japan

[73] Assignees: Neurosearch A/S, Glostrup, Denmark; Meiji Seika Kaisha, Ltd., Tokyo, Japan

[21] Appl. No.: 08/945,023

[22] PCT Filed: Apr. 17, 1996

[86] PCT No.: PCT/EP96/01606

§ 371 Date: Feb. 5, 1998

§ 102(e) Date: Feb. 5, 1998

[87] PCT Pub. No.: WO96/33194

PCT Pub. Date: Oct. 24, 1996

[30] Foreign Application Priority Data

Apr. 21, 1995 [DK] Denmark .................. 0460/95

[51] Int. Cl.$^6$ .......... A61K 31/415; A61K 31/44; A61K 31/425; A61K 31/505
[52] U.S. Cl. .......... 514/256; 544/331; 544/333; 546/269.4; 546/273.4; 548/304.7; 548/306.1; 548/131; 548/181; 548/247; 514/275; 514/338; 514/364; 514/365; 514/378; 514/394
[58] Field of Search ............... 548/304.7, 306.1, 548/131, 181, 247; 514/394, 256, 275, 338, 364, 365, 378; 544/331, 333; 546/269.4, 273.4

[56] References Cited

U.S. PATENT DOCUMENTS 5,554,630  9/1996  Teuber et al. ............ 514/338
5,554,632  9/1996  Teuber et al. ............ 514/338

FOREIGN PATENT DOCUMENTS 616807  9/1994  European Pat. Off. .

*Primary Examiner*—Laura L. Stockton
*Attorney, Agent, or Firm*—Birch, Stewart, Kolasch & Birch, LLP

[57] ABSTRACT

The present patent application discloses compounds having the formula

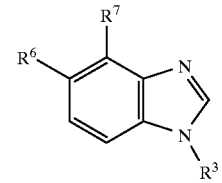

or a pharmaceutically acceptable salt thereof or an oxide thereof wherein $R^3$ is

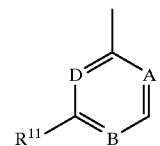

wherein A, B and D each is CH, or one or two of A, B and D is N and the others are CH;

$R^{11}$ is phenyl, benzimidazolyl, or monocyclic heteroaryl all of which may be substituted one or more times with substituents selected from alkyl, alkoxy, phenyl, halogen, $CF_3$, amino, nitro, cyano, acyl, acylamino, phenyl and monocyclic heteroaryl; and one of $R^6$ and $R^7$ is hydrogen and the other is furanyl or isoxazolyl each of which may be substituted one or more times with substituents selected from halogen, alkyl, alkoxy and phenyl. The compounds are useful for the treatment of various central nervous system disorders such as epilepsy and other convulsive disorders, anxiety, sleep disorders and memory disorders.

14 Claims, 6 Drawing Sheets

X is hydrogen or acetyl, A, B, D, and $R^{11}$ is as defined in the claims, and Cat. is tetrakis(triphenylphosphine)palladium(0).

A, B, D, R[11] is as defined in the claims, and Cat. is tetrakis(triphenylphosphine)-palladium(0).

A, B, and $R^{11}$ have the meanings set forth in the claims, Hal is halogen, Y is halogen or carboxy, $R^0$ is alkyl, phenyl, or heteroaryl, and Cat. is tetrakis(triphenylphosphine)-palladium(0).

Hal is halogen, D, A, B, $R^{11}$ have the meanings set forth in the claims, and Cat. is tetrakis(triphenyl-phosphine)palladium(0).

Hal is halogen, D, A, B, and R[11] have the meanings set forth in the claims, R is halogen or furanyl and Cat is tetrakis(triphenylphosphine)palladium(0).

D, A, B, and $R^{11}$ have the meanings set forth in the claims.

BENZIMIDAZOLE COMPOUNDS AND THEIR USE AS MODULATORS OF THE GABA A RECEPTOR COMPLEX This application is a 371 of PCT/EP96/01606 filed Apr. 17, 1996.

This invention relates to novel benzimidazole compounds, pharmaceutical compositions containing these compounds, methods of treating therewith, and to method of preparing such benzimidazole compounds. The novel compounds are useful in the treatment of central nervous system diseases and disorders, which are responsive to modulation of the $GABA_A$ receptor complex, such as for example anxiety, sleep disorders, memory disorders, and epilepsia or other convulsive disorders.

BACKGROUND OF THE INVENTION

Receptors for γ-aminobutyric acid (GABA), $GABA_A$ receptors are the most abundant inhibitory receptors in mammalian brain. The $GABA_A$ receptor are structurally constituted as macromolecular heteropentameric assemblies (combinations of αb, β, and γ/δ protein subunits). Several subtypes of such $GABA_A$ receptors have been described by techniques of modern molecular biology.

Each $GABA_A$ receptor complex comprises a chloride ion channel that controls chloride flux across the neuronal membrane, and multiple recognition sites for small modulatory molecules such as benzodiazepines, barbiturates, picrotoxin, and certain steroids. When GABA interacts with its receptor, the ion channel is opened, chloride influx is enhanced, the membrane is hyperpolarized and the cell becomes less responsive to excitatory stimuli. This GABA induced ion current can be regulated by diverse agents, including agents that interact with the benzodiazepine receptor or recognition site.

Agents that bind or interact with the modulatory sites on the $GABA_A$ receptor complex, such as for example the benzodiazepine receptor, can have either enhancing effect on the action of GABA, i.e. a positive modulatory effect of the receptor (agonists, partial agonists), an attenuating effect on the action of GABA, i.e. negative modulation of the receptor (inverse agonists, partial inverse agonists), or they can block the effect of both agonists and inverse agonists by competitive block (antagonists or ligands without intrinsic activity).

Agonists generally produce muscle relaxant, hypnotic, sedative, anxiolytic, and/or anticonvulsant effects, while inverse agonists produce proconvulsant, anti-inebriant, and anxiogenic effects. Partial agonists are characterized as compounds with anxiolytic effects but without or with reduced muscle relaxant, hypnotic and sedative effects, whereas partial inverse agonists are considered to be useful as cognition enhancers.

Numerous compounds belonging to different series of compounds having affinity for the benzodiazepine receptors have been synthesized during the last three decades. However, although the benzodiazepine receptor sites are still considered as very attractive biological sites for interfering with the CNS to treat various disorders and diseases, then nearly all previously synthesized compounds acting at these receptor sites have failed during clinical development because of unacceptable side effects.

The present invention provides novel benzimidazole compounds that interact with the benzodiazepine receptor of the $GABA_A$ receptor complex. The compounds of the present invention are valuable modulators of the $GABA_A$ receptor complex.

OBJECT OF THE INVENTION

It is an object of the present invention to provide novel benzimidazole compounds and pharmaceutically acceptable acid addition salts thereof, which are useful in the treatment of central nervous system disorders, diseases or ailments, which are responsive to the modulation of the $GABA_A$ receptor complex, and especially the positive modulation of the $GABA_A$ receptor complex.

Another object of the present invention is to provide pharmaceutical compositions comprising the novel benzimidazole compounds being useful for the above purposes. Still another object of the present invention is to provide a novel method of treating with the novel benzimidazole compounds.

A further object of the present invention is to provide a method of preparing the novel pharmaceutical compositions.

Additional objects will be obvious from the following description, and others will be obvious to one skilled in the art.

SUMMARY OF THE INVENTION

The invention then, inter alia, comprises the following, alone or in combination:

A compound having the formula:

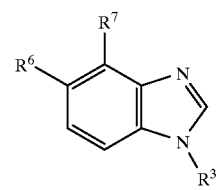

or a pharmaceutically acceptable salt thereof or an oxide thereof wherein $R^3$ is

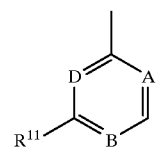

wherein
  A, B and D each is CH, or one or two of A, B and D is N and the others are CH;
  $R^{11}$ is phenyl, benzimidazolyl, or monocyclic heteroaryl all of which may be substituted one or more times with substituents selected from alkyl, alkoxy, phenyl, halogen, $CF_3$, amino, nitro, cyano, acyl, acylamino, phenyl and monocyclic heteroaryl; and
  one of $R^6$ and $R^7$ is hydrogen and the other is furanyl or isoxazolyl each of which may be substituted one or more times with substituents selected from halogen, alkyl, alkoxy and phenyl;
a compound as above, which is
  1-(3-(1-imidazolyl)phenyl)-5-(3-furanyl)benzimidazole,
  1-(3-(2-methyl-1-imidazolyl)phenyl)-5-(3-furanyl)benzimidazole, or
  1-(3-(5-pyrimidinyl)phenyl)-5-(3-furanyl)benzimidazole, or a pharmaceutically acceptable salt thereof or an oxide thereof;
a pharmaceutical composition comprising an effective amount of a compound as any above, or a pharmaceutically-acceptable addition salt thereof or an oxide thereof, together with at least one pharmaceutically-acceptable carrier or diluent; the use of a compound as any above for the preparation of a medicament for the treatment of a disorder or disease of a living animal body, including a human, which disorder or disease is responsive to modulation of the $GABA_A$ receptor complex of the central nervous system;

the use of a compound as any above for the preparation of a medicament for the treatment of a disorder or disease of a living animal body, including a human, which disorder or disease is responsive to positive modulation of the $GABA_A$ receptor complex of the central nervous system;

the use of a compound as any above for the preparation of a medicament for the treatment of a disorder or disease selected from anxiety, sleep disorders, memory disorders, epilepsy and any other convulsive disorder;

a method of treating a disorder or disease of a living animal body, including a human, which disorder or disease is responsive to modulation of the $GABA_A$ receptor complex of the central nervous system comprising administering to such a living animal body, including a human, in need thereof a therapeutically-effective amount of a compound as any above.

the method above, wherein a disorder or disease responsive to the positive modulation of the $GABA_A$ receptor complex is treated;

the method above, wherein anxiety, sleep disorders, memory disorders, epilepsy or any other convulsive disorder is treated; and the method above, wherein the active ingredient is administered in form of a pharmaceutical composition thereof, in which it is present together with a pharmaceutically-acceptable carrier or diluent. Halogen is fluorine, chlorine, bromine, or iodine.

Alkyl means a straight chain or branched chain of from one to eight carbon atoms or cyclic alkyl of from three to seven carbon atoms, including but not limited to, methyl, ethyl, propyl, isopropyl, butyl, isobutyl, t-butyl, pentyl, hexyl, cyclopropyl, cyclobutyl, cyclopentyl, cyclohexyl; methyl, ethyl, propyl, isopropyl and t-butyl are preferred groups.

Alkoxy means —O-alkyl, wherein alkyl is as defined above.

Acyl means —(C=O)—H or —(C=O)-alkyl, wherein alkyl is as defined above.

Acylamino is acyl-NH— wherein acyl is as defined above.

Amino is —$NH_2$ or —NH-alkyl or —N—$(alkyl)_2$, wherein alkyl is as defined above.

Monocyclic heteroaryl is a 5- or 6-membered heterocyclic monocyclic group. Such a monocyclic heteroaryl group includes, for example, oxazol-2-yl, oxazol-4-yl, oxazol-5yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidyl, 4-pyrimidyl, 5-pyrimidyl, 3-pyridazinyl, 4-pyridazinyl, 2-pyrazinyl,1-pyrazolyl, 3-pyrazolyl, and 4-pyrazolyl.

Examples of pharmaceutically-acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesuffonate, stearate, succinate, glutamate, glycollate, toluene-p-sulphonate, formate, malonate, naphthalene-2-sulphonate, salicylate and the acetate for example.

Other acids such as oxalic acid, while not in themselves pharmaceutically acceptable may be useful in the preparation of salts useful as intermediates in obtaining compounds of the invention and their pharmaceutically acceptable acid addition salts. Such salts are formed by procedures well known in the art.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention exist in (+) and (−) forms as well as in racemic forms. Racemic forms can be resolved into the optical antipodes by known methods, for example, by separation of diastereomeric salts thereof, with an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallization of d- or I- (tartrates, mandelates, or camphorsulphonate) salts for example. The compounds of the instant invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolvation of optical isomers, known to those skilled in the art may be used, and will be apparent to the average skilled in the art. Such methods include those discussed by J. Jaques, A. Collet, and S. Wilen in "Enantiomers, Racemates, and Resolutions", John Wiley and Sons, New York (1981).

The compounds of the invention may be prepared in numerous ways.

The compounds of the invention and their pharmaceutically acceptable derivatives may thus be prepared by any method known in the art for the preparation of compounds of analogous structure and as shown in the representative examples which follows.

Figure 1:
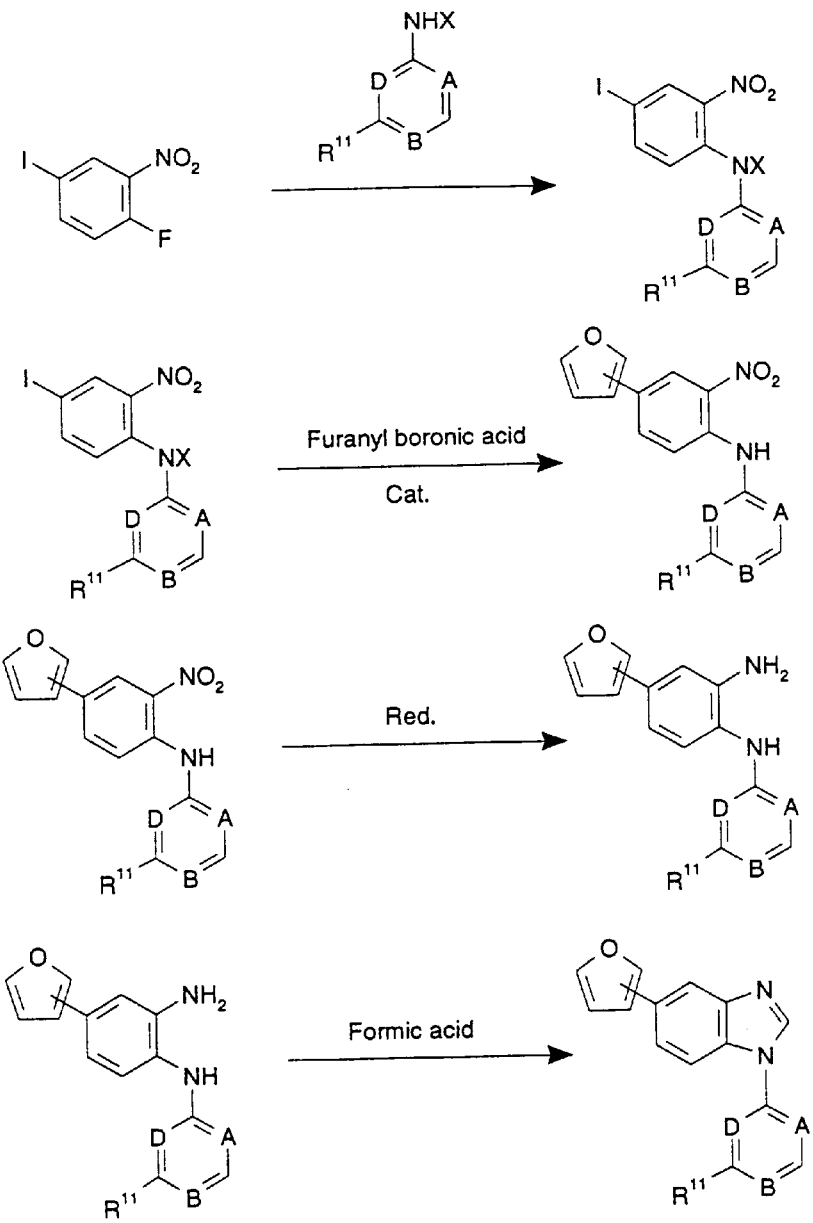
FIGS. 1–6 describe methods for the preparation of compounds of the invention wherein $R^6$ is furanyl or isoxazolyl and $R^7$ is hydrogen. Compounds of the invention wherein $R^7$ is furanyl or isoxazolyl and $R^6$ is hydrogen can be synthesized analogously.
Figure 2:
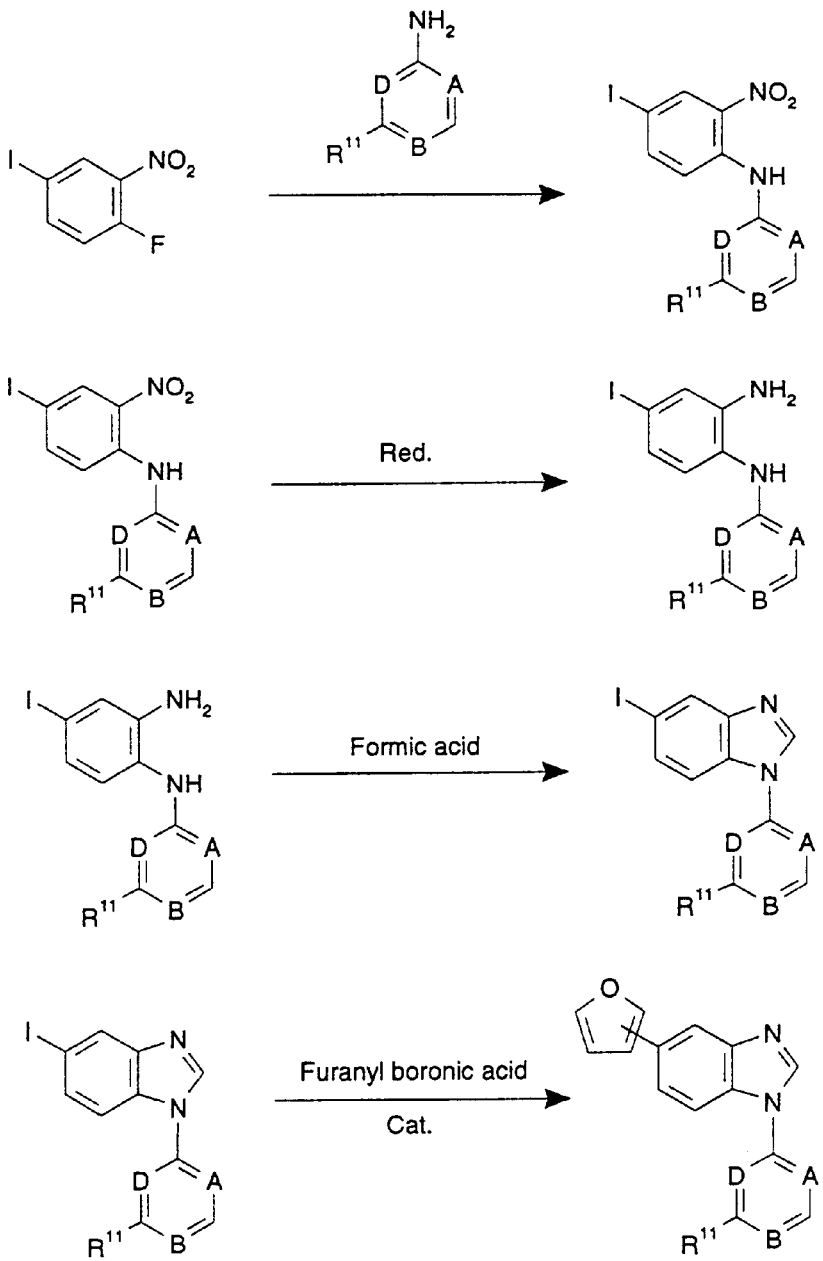
Figure 3:
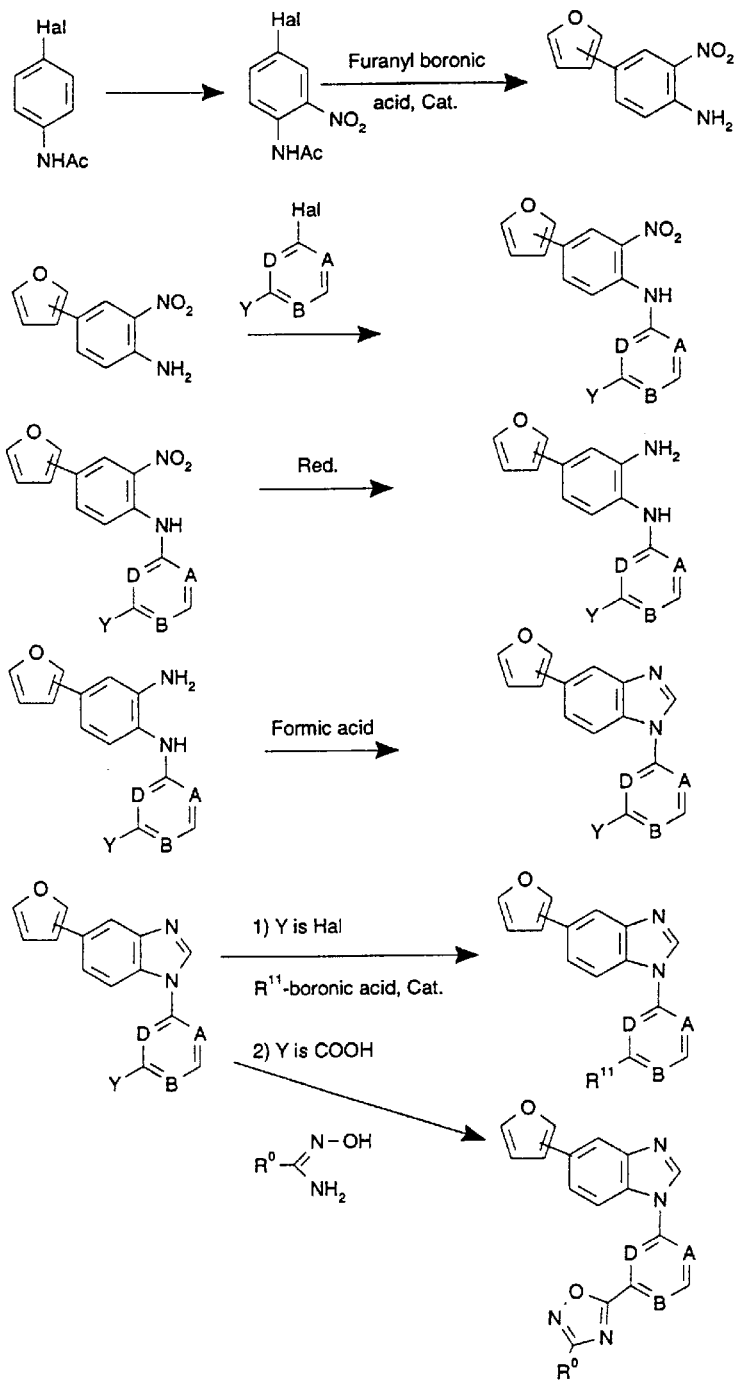
Figure 4:
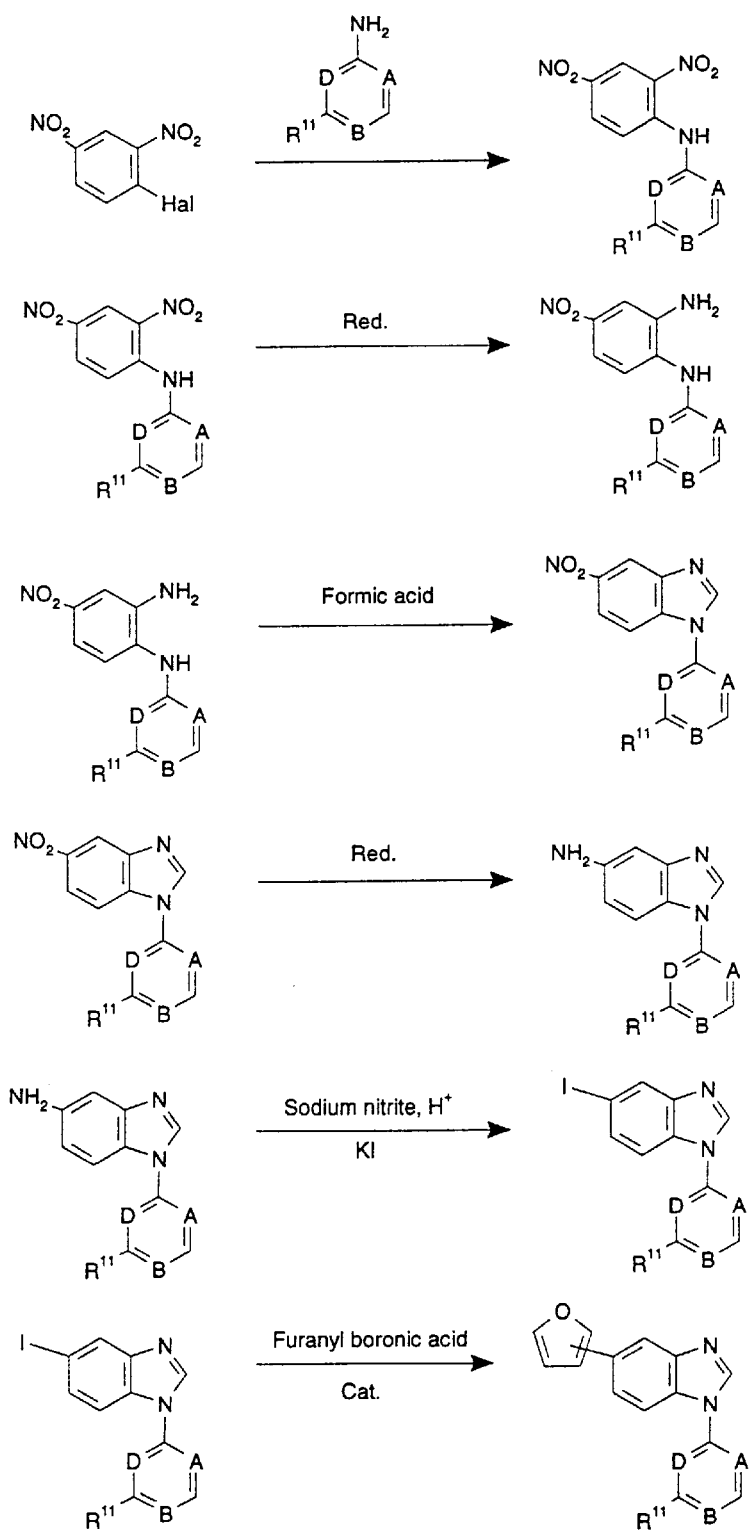
Figure 5:
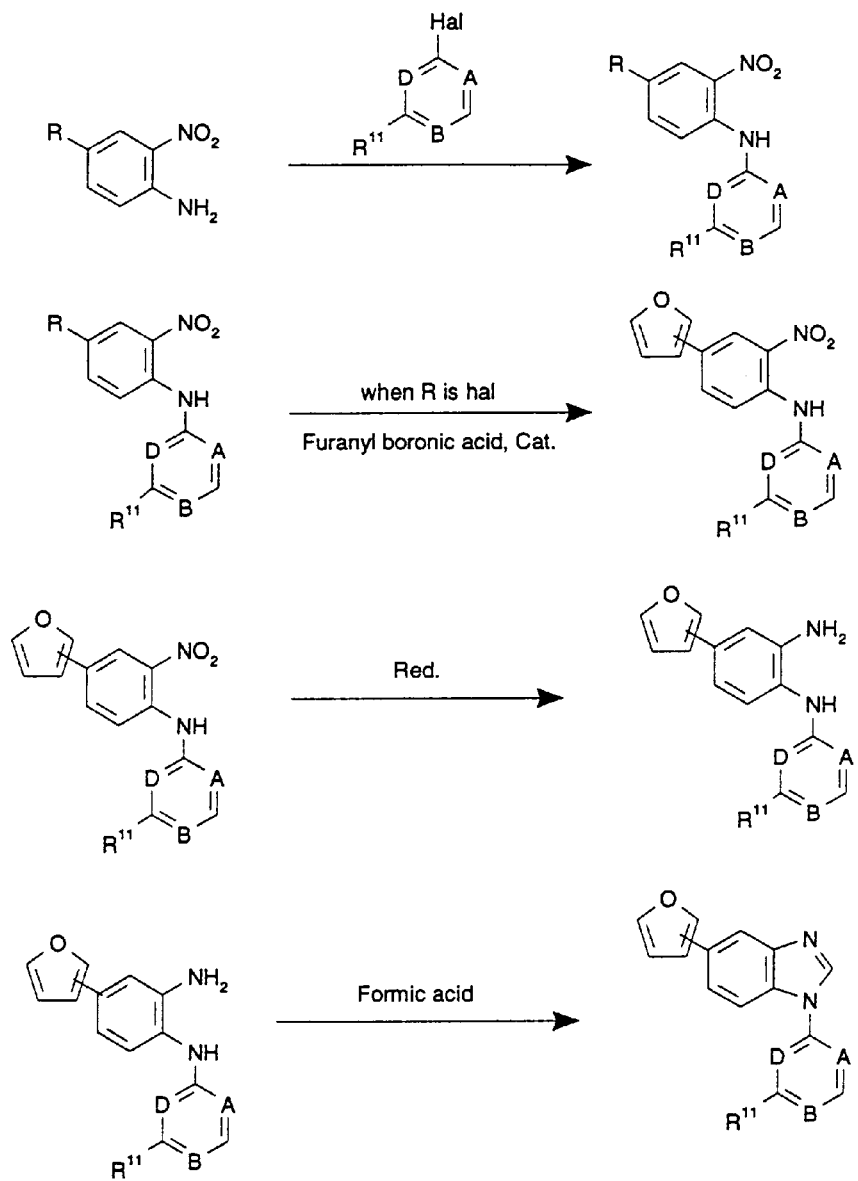
Figure 6:
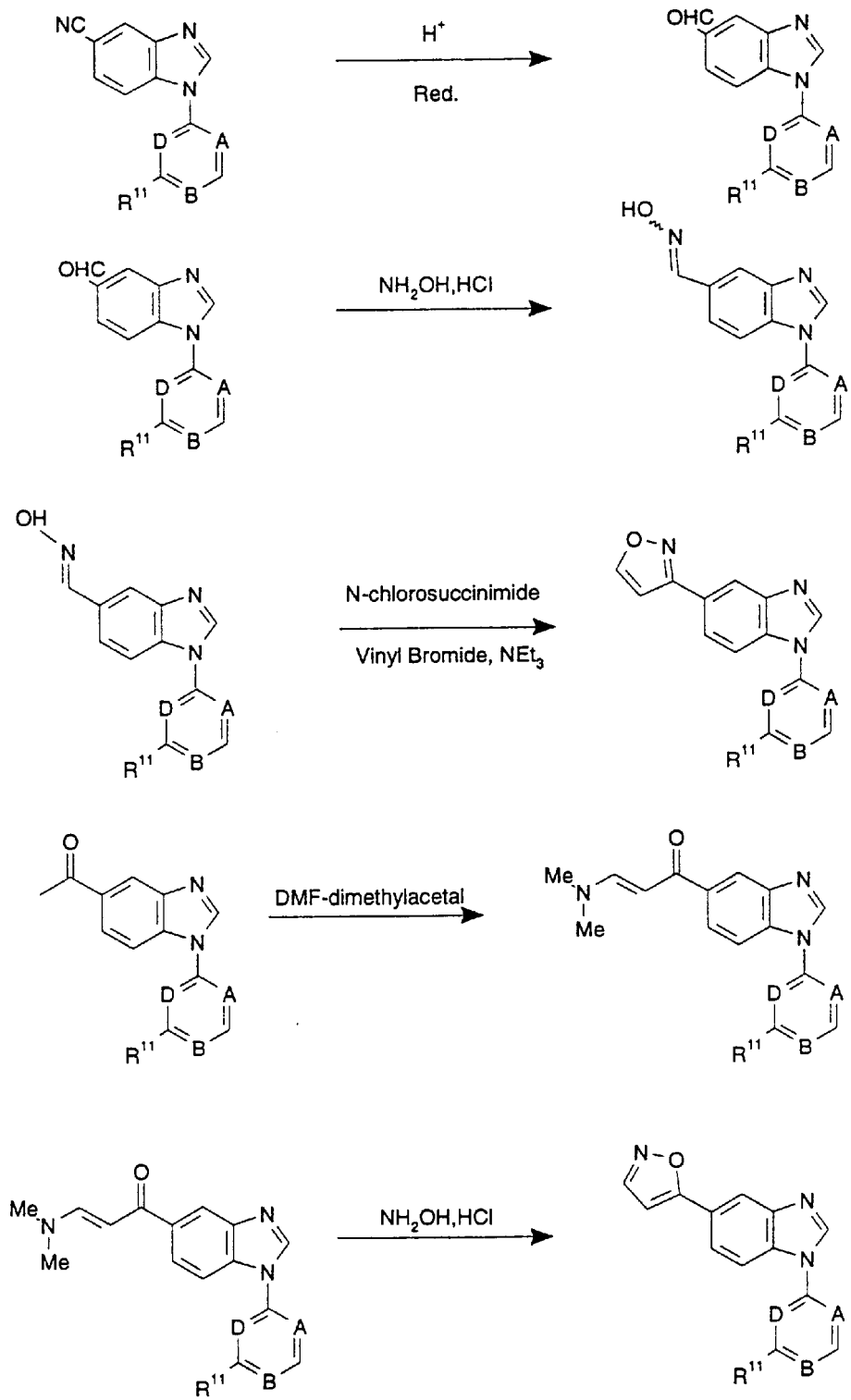

Starting materials for the processes described in the present patent application are known or can be prepared by known processes from commercially available chemicals.

The products of the reactions described herein are isolated by conventional means such as extraction, crystallization, distillation, chromatography and the like.

Biology 4-aminobutyric acid (GABA) is the major inhibitory neurotransmitter and has been shown to act throughout both the central and peripheral nervous system. At present two types of GABA receptors are known, the $GABA_A$ and the $GABA_B$ receptors. Recent molecular biology has demonstrated that the $GABA_A$ receptors can be subdivided into numerous subreceptors consistant with the selective and or partial pharmacological effects observed with certain benzodiazepine receptor ligands as opposed to the unselective effects observed for the classical benzodiazepine receptor ligands such as for example diazepam. Activation of GABA receptors leads to alternations in membrane potential (hyperpolarization). The $GABA_A$ receptors are associated with chloride influx through its associated and integrated chloride channel, whereas $GABA_B$ receptor activation indirectly alters potassium and calcium channels as well as modifies second messenger production. The $GABA_A$ recognition sites can be activated by GABA, muscimol; and isoguvacine for example, but not by $GABA_B$ agonists such as for example baclofen. The modulatory $GABA_A$ recognition site at the benzodiazepine receptor sites can be selectively radiolabelled with $^3$H-flunitrazepam. The affinity of various potential ligands for the benzodiazepine receptor sites can thus be evaluated by estimating the ability of test compounds to displace $^3$H-flunitrazepam.

Method

Tissue Preparation:

Preparations are performed at 0–4° C. unless otherwise indicated. Cerebral cortex from male Wistar rats (150–200 g) is homogenized for 5–10 sec in 20 ml Tris-HCl (30 mM, pH 7.4) using an Ultra-Turrax homogenizer. The suspension is centrifuged at 27,000× g for 15 min and the pellet is washed three times with buffer (centrifuged at 27,000× g for 10 min). The washed pellet is homogenized in 20 ml of buffer and incubated on a water bath (37° C.) for 30 min to remove endogenous GABA and then centrifuged for 10 min at 27,000× g. The pellet is then homogenized in buffer and centrifuged for 10 min at 27,000× g. The final pellet is resuspended in 30 ml buffer and the preparation is frozen and stored at −20° C.

Assay:

The membrane preparation is thawed and centrifuged at 2° C. for 10 min at 27,000× g. The pellet is washed twice with 20 ml 50 mM Tris-citrate, pH 7.1 using an Ultra-Turrax homogenizer and centrifuged for 10 min at 27,000× g. The final pellet is resuspended in 50 mM Tris-citrate, pH 7.1 (500 ml buffer per g of original tissue), and then used for binding assays. Aliquots of 0.5 ml tissue are added to 25 μl of test solution and 25 μl of $^3$H-FNM (1 nM, final concentration), mixed and incubated for 40 min at 2° C. Non-specific binding is determined using clonazepam (1 μM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

The test value is calculated as the $IC_{50}$ (the concentration (nM) of the test substance which inhibits the specific binding of $^3$H-FNM by 50%).

Test results obtained by testing selected compounds of the present invention appear from the following table:

TABLE

| Test compound: | $IC_{50}$ (nM) |
| --- | --- |
| 1-(3-(1-Imidazolyl)-phenyl)-5-(3-furanyl)benzimidazole | 0.4 |
| 1-(3-(2-Methyl-1-imidazolyl)-phenyl)-5-(3-furanyl)benzimidazole | 0.4 |

Pharmaceutical Compositions

While it is possible that, for use in therapy, a compound of the invention may be administered as the raw chemical, then it is preferable to present the active ingredient as a pharmaceutical formulation.

The invention thus further provides a pharmaceutical formulation comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing one (1) milligram of active ingredient or, more broadly, 0.01 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules.

A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting vax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting vax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water propylene glycol solutions. For example, parenteral injection liquid preparations can be formulated in solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of this invention are extremely useful in the treatment of disorders or diseases of a living animal body due to their affinity for the benzodiazepine binding site of the $GABA_A$ receptor. These properties make the compounds of this invention extremely useful in the treatment of convulsions, anxiety, sleep disorders, memory disorders as well as other disorders sensitive to modulation of the GABA$_A$ receptor. The compounds of this invention may accordingly be administered to a subject, including a human, in need of treatment, alleviation, or elimination of a disorder or disease associated with the GABA$_A$ receptors. This includes especially convulsions, anxiety, sleep disorders and memory disorders.

Suitable dosage range are 0.01–100 milligrams daily, 0.1–50 milligrams daily, and especially 0.1–30 milligrams daily, dependent as usual upon the exact mode of administration, form in which administered, the indication towards which the administration is directed, the subject involved and the body weight of the subject involved, and further the preference and experience of the physician or veterinarian in charge.

The following examples will illustrate the invention further; however they are not to be construed as limiting. The compounds of the invention prepared in the following examples are listed in tables 1–2 on pages 41–43.

Example 1

4-Fluoro-1-iodo-3-nitrobenzene (1c): A suspension of 4-fluoro-3-nitroaniline (100 g, 0.64 mol) in conc. hydrochloric acid (500 ml) is cooled to −20° C. A solution of sodium nitrite (48.6 g, 0.7 mol) in 100 ml of water is added with stirring, keeping the temperature below −15° C. Following the addition the mixture is stirred for 45 min. at −20-(−15)° C. To the resulting solution a solution of potassium iodide (132.8 g, 0.8 mol) in 260 ml of water is added at such a rate that the temperature is kept below 0° C. The mixture is stirred until the evolution of nitrogen has ceased. Aqueous sodium sulfite (200 ml, 1 M) is added and the mixture is extracted with diethyl ether. The etheral extract is washed twice with ice-cold 1 M aqueous sodium hydroxide and twice with brine. Finally the extract is dried over magnesium sulfate, concentrated and purified by column-chromatography on silica gel using a mixture of ethyl acetate and petroleum ether (1:9) as the eluent. 1cis isolated as an oil, which crystallizes in the refrigerator. Yield: 132.6 g (78%).

Example 2

3-(5-Pyrimidyl)aniline (2b): A suspension of 5-bromopyrimidine (1 5 g, 94.3 mmol), 3-aminophenylboronic acid hemisulfate (19.3 g, 104 mmol), sodium bicarbonate (39.6 g, 472 mmol) and tetrakis (triphenylphosphine)palladium(0) (1 g) in a mixture of water (75 ml) and dimethoxyethane (150 ml) is heated to 80° C. under a stream of nitrogen over night. After cooling the mixture is poured into ice-water. The precipitate is filtered off, washed with water and dried to yield 2b (15 g, 93%). Mp 164–165° C.

3-(2-Thiazolyl)aniline (2t) was prepared analogously from 2-bromothiazole. The product was purified by column-chromatography using a mixture of ethyl acetate and petroleum ether (1:1) as the eluent. Yield: 25%. Mp 43–49° C.

Example 3

3-(1-Imidazolyl)aniline (2d): A mixture of 1-iodo-3-nitrobenzene (90 g, 0.36 mol), imidazole (54 g, 0.79 mol), potassium carbonate (54 g, 0.39 mol) and finely divided copper powder (1 g) is heated to 200° C. The melt is stirred for 2 hours under nitrogen. During the reaction water vapor is trapped by molecular sieves, placed between the reation vessel and the condenser. Following the reaction the mixture is cooled to 100° C. and water is added. The mixture is allowed to cool to room temperature and the crude product is filtered off and dried. Recrystallization from toluene (200–250 ml) affords pure 3-(1-imidazolyl)nitrobenzene (54.2 g, 79%). Mp 101–102° C.

To 3-(1-imidazolyl)nitrobenzene (51.6 g, 0.27 mol) in acetic acid (500 ml) is added palladium catalyst (5 g 5% Pd on activated carbon) and the mixture is hydrogenated under pressure (P$_{start}$: 4 bar) until the hydrogen uptake has ceased. The mixture is filtered through celite and the filtrate is evaporated to dryness to leave 2d as a light-brown oil. Yield: 40.4 g (93%).

N-Acetyl 3-(1-imidazolyl)aniline (2e): 2d (5.88 g, 37 mmol) is stirred in acetic anhydride (30 ml) at ambient temperature for 1 hour. The mixture is poured into ice-water and rendered alkaline by addition of aqueous sodium hydroxide (12M). The product is filtered off, washed with water and dried to yield 2e (6.34 g, 85%). Mp 181–183° C.

Example 4

3-(2-Pyridyl)aniline (2f): To a solution of 2-(3-nitrophenyl)pyridine (prepared as described in J. Chem. Soc. 1958 p. 1759) (12.7 g, 63.5 mmol) in abs. ethanol is added palladium catalyst (1.3 g 5% Pd on activated carbon) and the mixture is hydrogenated at ambient pressure until the hydrogen uptake has ceased. The mixture is filtered through celite and the filtrate is concentrated under reduced pressure. The residue is purified by column-chromatography on silica gel using a mixture of ethyl acetate and petroleum ether (9:1) as the eluent to afford 2f (9.5 g, 88%) as a light brown oil.

5-(3-Furanyl)-2-(3-carboxyphenyl)aminoaniline (13r) was prepared analogously from 12r (Example 21). Ethyl acetate was used as the eluent for the chromatographic workup. Yield: 91%. Mp 211–212° C.

Example 5

2-(Dimethylamino)pyrimidine: A solution of 2-chloropyrimidine (5 g, 43.65 mmol) in dry THF (50 ml) is saturated with gaseous dimethylamine. The mixture is stirred at ambient temperature for 1 hour followed by evaporation of solvent. The residue is partitioned between water and ethyl acetate. The aqueous phase is extracted with ethyl acetate. The combined organic phases are dried over sodium sulfate and evaporated to leave the product as a brownish oil. Yield 5.07 g (94%).

5-Bromo-2-(dimethylamino)pyrimidine. The above product (5.07 g, 41.22 mmol) is dissolved in glacial acetic acid (25 ml) and bromine (2.15 ml, 41.95 mmol) is added. The mixture is stirred for 30 min. at ambient temperature and then poured into ice-water. The mixture is rendered alkaline by addition of 10 M sodium hydroxide. The product is filtered off, washed with water and dried to yield 4.72 g (57%). Mp 162–164° C.

3-(2-(Dimethylamino)-5-pyrimidyl)aniline (2h): A mixture of 5-bromo-2(dimethylamino)pyrimidine (6.76 g, 33.17 mmol), 3-aminophenylboronic acid hemisulfat (7.4 g, 39.78 mmol) potassium carbonate (13.73 g, 99.49 mmol), 1,3-propanediol (12 ml, 166 mmol) and tetrakis (triphenylphosphine)palladium(0) (0.2 g) in a mixture of water (30 ml) and dimethoxyethane (60 ml) is heated to 80° C. under nitrogen over night. After cooling the mixture is diluted with water and ethyl acetate and is filtered through a fluted filterpaper. The layers are separated and-the aqeous phase is extracted once with ethyl acetate. The combined organic phases are dried over sodium sulfate and evaporated to dryness. The residue is triturated with a mixture of ethyl acetate and petroleum ether (1:1) to leave crystalline 2h (5.26 g, 74%). Mp 115.5–117° C.

N-Acetyl 3-(2-methylimidazol-1-yl)aniline (2j): 3-(2-Methylimidazol-1-yl)aniline (11 g, 63.6 mmol) is added in portions to acetic anhydride (100 ml) at ambient temperature. After stirring for 1 hour the mixture is poured into water (300 ml). The resulting solution is cooled in an ice-bath and rendered alkaline with aqueous sodium hydroxide (12M). The product is filtered off, washed thoroughly with water and dried to yield 2j (12.3 g, 97%). Mp 238–240° C.

Example 6

1-(3-Nitrophenyl)pyrrol: A mixture of 3-nitroaniline (15 g, 0.11 mmol), 2,5-dimethoxytetrahydrofuran (42 ml, 0.33 mol) and a catalytic amount of pTSA in dry toluene (150 ml) is heated to reflux for 2 hours. After cooling the mixture is concentrated under reduced pressure and the residue is purified by column-chromatography on silica gel using a mixture of ethyl acetate and petroleum ether (1:1) as the eluent. Yield: 16 g (78%). Mp 65–70° C.

3-(1-Pyrrolyl)aniline: To a suspension of the above product (1 6 g, 85.1 mmol) in glacial acetic acid (100 ml) is added palladium catalyst (1.5 g 5% Pd on activated carbon) and the mixture is hydrogenated ($P_{start}$=4 bar) until the hydrogen uptake has ceased. The mixture is filtered through celite and the solvent is removed by evaporation. The resulting crude product is used for the next step without purification.

N-Acetyl 3-(1-pyrrolyl)aniline (2k): To the above product is added acetic anhydride (40 ml) and the mixture is stirred at ambient temperature over night. The mixture is poured into water. The crude product is filtered off, washed with water and dried. Recrystallization from a mixture of water and ethanol (3:2) affords pure 2k. Yield: 9.93 g (58%). Mp 134–136° C.

Example 7

3-(2-Aminopyrimid-5-yl)aniline (2l): A mixture of 2-(acetamino)-5-bromopyrimidine (5.4 g, 25 mmol), 3-aminophenylboronic acid hemisulfate (5.58 g, 30 mmol), potassium carbonate (10.4 g, 75 mmol), 1,3-propanediol (9 ml, 0.13 mmol) and tetrakis(triphenylphosphine)palladium (0) (0.5 g) in a mixture of water (25 ml) and dimethoxyethane (50 ml) is stirred at 80° C. under a stream of nitrogen over night. After cooling the mixture is poured into ice-water. The product (deacetylated during the reaction) is filtered off, washed with water and dried to yield 2l (4.19 g, 90%). Mp 171172° C.

Example 8

N-Acetyl N-(3-(1-imidazolyl)phenyl)-2-nitro-4-iodoaniline (6c): A solution of 2e from Example 3 (30 g, 0.15 mol) in dry DMF (200 ml) is cooled to 0° C. under nitrogen. Sodium hydride (7.2 g of a 60% dispersion in mineral oil) is added portionwise. When the evolution of hydrogen has ceased a solution of 1c from Example 1 (52 g, 0.19 mol) in 50 ml DMF is added. The mixture is stirred at 120° C. for 5 hours and left at ambient temperature over night. The reaction mixture is poured into four volumes of water and the crude product is filtered off. Purification on silica gel using a mixture of ethyl acetate and petroleum ether (3:17) as the eluent affords pure 6c as an oil (17 g, 25%).

Example 9

N-(3-(2-Methyl-1-imidazolyl)phenyl)-2-nitro-4-iodoaniline (6j): To a solution of 2j from Example 5 (2 g, 9.3 mmol) in dry N-methyl-2-pyrrolidone (20 ml) is added sodium hydride (0.37 g of a 60% dispersion in mineral oil) in portions at 0° C. under nitrogen. The mixture is stirred for 1 hour, the last 30 min. at room-temperature. 1c from Example 1 (2.67 g, 10 mmol) is added and the temperature is raised to 40–50° C. over night. After cooling the mixture is poured into water (100 ml) and extracted with dichloromethane. The organic phase is extracted with 4M hydrochloric acid. The acidic extract is cooled in ice, rendered alkaline by addition of sodium hydroxide (12M) and extracted with dichloromethane. The organic phase is dried over magnesium sulfate and evaporated to dryness. The residue is extracted with a mixture of dichloromethane and diethyl ether (1:1). This extract is concentrated under reduced pressure and the residue is dissolved in dimethoxyethane (60 ml). Aqueous sodium hydroxide (28 ml, 1 M) is added and the mixture is stirred at ambient temperature over night. The mixture is poured into water (200 ml) and a small volume of ethanol is added with stirring. The product is filtered off, washed with water and dried to leave 6j (2 g, 51%). Mp 135–136° C.

N-(3-(1-Pyrrolyl)phenyl)-2-nitro-4-nitroaniline (6k) was prepared analogously from 1c (Example 1) and 2k (Example 6). Yield: 30%. Mp 116–118° C.

Example 10

N-(3-(2-(Dimethylamino)pyrimid-5-yl)phenyl-2-nitro-4-iodoaniline hydrofluoride (6h): A mixture of 1c from Example 1 (3 g, 11.2 mmol) and 2h from Example 5 (2.4 g, 11.2 mmol) in dry N-methyl-2-pyrrolidone (10 ml) is stirred under nitrogen at 120–135° C for 6 hours. The mixture is allowed to cool to room temperature and stirring is continued over night. To the resulting suspension is added water. The product is filtered off, dried and washed with ethyl acetate to afford 6h (3.46 g, 64%). Mp 202–203° C.

N-(3-(2-aminopyrimid-5-yl)phenyl)-2-nitro-4-iodoaniline hydrofluoride (6l) was prepared analogously from 1c (Example 1) and 2l (Example 7). Yield: 79%. Mp 236–238° C.

N-(3-(1-Pyrazolyl)phenyl)-4-iodo-2-nitroaniline (6m) was prepared analogously from 1c (Example 1) and 2m (Example 16). The base was liberated by treatment with aqueous sodium carbonate. Yield: 23%. Mp 165–166° C.

N-(3-(2-Methylthiazol-4-yl)phenyl)-4-iodo-2-nitroaniline (6n) was prepared analogously from 1c (Example 1) and 2n (Example 17). Yield: 32%. Mp 137–138° C.

N-(3-(5-Pyrimidyl)phenyl)-4-iodo-2-nitroaniline (6b) was prepared analogously from 1c (Example 1) and 2b (Example 2). Yield 79%. Mp 214–217° C.

N-(3-(2-Pyridyl)phenyl)-4-iodo-2-nitroaniline (6f) was prepared analogously from 1c (Example 1) and 2f (Example 4). Yield: 40%. Mp 195–196° C.

Example 11

N-(3-(1-Imidazolyl)phenyl)-4-(3-furanyl)-2-nitroaniline (7c): A mixture of 6c from Example 8 (17 g, 38 mmol), 3-furanylboronic acid (5.6 g, 50 mmol), 1,3-propanediol (14 ml, 0.17 mol), potassium carbonate (15.7 g, 0.11 mol) and tetrakis(triphenylphosphine)palladium(0) (0.5 g) in a mixture of water (60 ml) and dimethoxyethane (120 ml) is refluxed under nitrogen for 4 hours. After cooling the mixture is poured into water (800 ml) and is stirred at 0° C. until the precipitation of oily crystals is complete. This crude product (a mixture of acetylated and deacetylated product) is filtered off and dissolved in dimethoxyethane (200 ml). Aqueous sodium hydroxide (114 ml, 1 M) is added and the mixture is stirred at ambient temperature over night. The mixture is poured into water (500 ml) and the product is filtered off, washed with water and dried. Yield: 13.1 g (100%). Mp 129–131° C.

N-(3-(1-Imidazolyl)phenyl)-4-(2-furanyl)-2-nitroaniline (7o) was prepared analogously from 6c (Example 8) and 2-furanylboronic acid. Yield: 77%. Mp 147–149° C.

Example 12

N-(3-(2-Methylimidazol-1-yl)phenyl)-4-(3-furanyl)-2-nitroaniline (7j): A mixture of 6j from Example 9 (1 g, 2.38 mmol), 3-furanylboronic acid (0.4 g, 3.57 mmol), potassium carbonate (1 g, 7.25 mmol), 1,3-propanediol (0.9 ml, 11.2 mmol) and tetrakis(triphenylphosphine)palladium(0) (50 mg) in a mixture of dimethoxyethane (7 ml) and water (3.5 ml) is heated to reflux under nitrogen for 4 hours. After cooling the mixture is poured into water (30 ml) and extracted with ethyl acetate. The organic phase is dried over magnesium sulfate and concentrated under reduced pressure. The residue is purified by column-chromatography on silica gel using a mixture of ethanol and ethyl acetate (1:4) as the eluent. Yield: 0.8 g (93%). The product was isolated as an oil.

N-(3-(2-(Dimethylamino)pyrimid-5-yl)phenyl)-4-(3-furanyl)-2-nitroaniline (7h) was prepared analogously from 6h (Example 10) in 87% yield. Mp 181–182° C.

N-(3-(2-(Dimethylamino)pyrimid-5-yl)phenyl)-4-(2-furanyl)-2-nitroaniline (7m) was prepared analogously from 6h (Example 10) and 2-furanylboronic acid in 89% yield. Mp 160–161° C.

N-(3-(1-Pyrrolyl)phenyl)-4-(3-furanyl)-2-nitroaniline (7k) was prepared analogously from 6k (Example 9) and 3-furanylboronic acid. Yield: 86%. Mp 129–131° C.

N-(3-(1-Pyrrolyl)phenyl)-4-(2-furanyl)-2-nitroaniline (7n) was prepared analogously from 6k (Example 9) and 2-furanylboronic acid. Yield: 83%. Isolated as a brownish-red oil.

N-(3-(2-Aminopyrimid-5-yl)phenyl)-4-(3-furanyl)-2-nitroaniline (7l) was prepared analogously from 6l (Example 10) and 3-furanylboronic acid in quantitative yield. Mp 185–186° C.

N-(3-(2-Aminopyrimid-5-yl)phenyl)-4-(2-furanyl)-2-nitroaniline (7p) was prepared analogously from 6l (Example 10) and 2-furanylboronic acid in quantitative yield. Mp 178–180° C.

1-(3-(5-Pyrimidyl)phenyl)-5-(3-furanyl)benzimidazole (9b) was prepared analogously from 11b (Example 15) and 3-furanylboronic acid. A mixture of dichloromethane and methanol (19:1) was used as eluent for the chromatographic purification. Yield: 48%. Mp 216–218° C.

1-(3-(2-Methylthiazol-4-yl)phenyl)-5-(3-furanyl) benzimidazole (9N) was prepared analogously from 11n (Example 15) and 3-furanylboronic acid. A mixture of ethyl acetate and petroleum ether (1:1) was used as eluent for the chromatographic purification. Yield: 73%. Mp 136–138° C.

1-(3-(1-Pyrazolyl)phenyl)-5-(3-furanyl)benzimidazole (9M) was prepared analogously from 11m (Example 15) and 3-furanylboronic acid. Yield: 64%. Mp 170–173° C.

1-(3-(2-Pyridyl)phenyl)-5-(2-furanyl)benzimidazole (9f) was prepared analogously from 11f (Example 15) and 2-furanylboronic acid. The crude product was purified by treatment of an ethanolic solution with activated carbon. Yield: 42%. Mp 135–1 36° C.

1-(3-(3-Furanyl)phenyl)-5-(3-furanyl)benzimidazole (9q) was prepared analogously from 14q (Example 15). Yield: –15%. Mp 149–150° C.

N-(2-(1-Imidazolyl)pyridin-6-yl)-4-(3-furanyl)-2-nitroaniline (16c) was prepared analogously from 16a (Example 25). Chromatographic workup was omitted. The product crystallizes quantitatively upon addition of water. Mp 173–174° C.

Example 13

N-(3-(1-Imidazolyl)phenyl)-2-amino-4-(3-furanyl) aniline (8c): To a solution of 7c from Example 11 (13 g, 37.6 mmol) in ethanol (25 ml) is added ammonium chloride (6.03 g, 113 mmol) and sodium sulfide nonahydrate (27.05 g, 113 mmol). The mixture is heated to reflux for 1 hour. After cooling the mixture is poured into 700 ml of water. The product is filtered off, washed with water and air-dried to yield 8c (8.7 g, 73%). Mp 188–189° C.

N-(3-(2-Methylimidazol-1-yl)phenyl)-2-amino-4-(3-furanyl)aniline (8j) was prepared analogously from 7j (Example 12) in quantitative yield. Mp 98–99° C.

N-(3-(1-Pyrrolyl)phenyl)-2-amino-4-(3-furanyl)aniline (8k) was prepared analogously from 7k (Example 12). Yield: 80%. Mp 194–195° C.

N-(3-(1-Imidazolyl)phenyl)-2-amino-4-(2-furanyl) aniline (8o) was prepared analogously from 7o (Example 11). Yield: 94%. Mp 191–194° C.

N-(3-(1-Pyrrolyl)phenyl)-2-amino-4-(2-furanyl)aniline (8n) was prepared analogously from 7n (Example 12). Yield: 77%. Mp 163–164° C.

N-(3-(2-(Dimethylamino)pyrimid-5-yl)phenyl)-2-amino-4-(3-furanyl)aniline (8h) was prepared analogously from 7h (Example 12). Isolated as an oil.

N-(3-(2-(Dimethylamino)pyrimid-5-yl)phenyl)-2-amino-4-(2-furanyl)aniline (8m) was prepared analogously from 7m (Example 12). Isolated as an oil.

N-(3-(1-Pyrazolyl)phenyl-2-amino-4-iodoaniline (10m) was prepared analogously from 6m (Example 10). Yield: 75%. Mp 134–135° C.

N-(3-(5-Pyrimidyl)phenyl)-2-amino-4-iodoaniline (10b) was prepared analogously from 6b (Example 10). Yield 82%. Mp 166–169° C.

N-(3-(2-Pyridyl)phenyl)-2-amino-4-iodoaniline (10f) was prepared analogously from 6f (Example 10). The product was used directly for the next step. See Example 15.

N-(3-(2-Methylthiazol-4-yl)phenyl-2-amino-4-iodoaniline (10n) was prepared analogously from 6n (Example 10). Yield: 73%. Mp 151–152° C.

N-(3-Bromophenyl)-2-amino-4-(3-furanyl)aniline in mixture with N-(3-iodophenyl)-2amino-4-(3-furanyl)aniline (13q) was prepared analogously from 12q (Example 20). The product mixture was isolated as an oil. Yield: ~76%.

N-(3-(2-Thiazolyl)phenyl)-2-amino-4-nitroaniline (20t) was prepared analogously from 19t (Example 27). Yield: 96%. Mp 146–159° C.

Example 14

N-(3-(2-Aminopyrimid-5-yl)phenyl)-2-amino-4-(2-furanyl)aniline (8l) To a suspension of 7p from Example 12 (0.87 g, 2.33 mmol) in ethanol (10 ml) is added 0.1 g palladium catalyst (5% Pd on activated carbon) and the mixture is hydrogenated at ambient pressure until the hydrogen uptake has ceased. The mixture is filtered through celite, which is washed with ethanol and DMF successively. The filtrate is evaporated under reduced pressure, and the residue is triturated with water. The product is filtered off, washed with water and air-dried to yield 8l (0.5 g, 63%). Mp 211–212° C.

N-(3-(2-Aminopyrimid-5-yl)phenyl)-2-amino-4-(3-furanyl)aniline (8p): 71 (Example 12) is hydrogenated as described above to yield 8p (43%). Mp 208–209° C.

Example 15

1-(3-(1-Imidazolyl)phenyl)-5-(3-furanyl)benzimidazole (9c): A solution of 8c from Example 13 (8.7 g, 27.5 mmol) in formic acid (100 ml) is heated to reflux for 30 min. After cooling the mixture is poured into water (500 ml) and rendered alkaline by addition of aqueous sodium hydroxide (12M). The crude product is filtered off, washed with water and air-dried. A solution of this crude product in a mixture of ethanol (200 ml) and dichloromethane (400 ml) is treated with activated carbon at reflux for 15 min. The mixture is filtered through celite and the filtrate is concentrated under reduced pressure until onset of precipitation. Precipitation is completed by cooling in an ice-bath. The product is filtered off and dried. Yield: 7.5 g (84%) Mp. 203–204° C.

1-(3-(2-(Dimethylamino)pyrimid-5-yl)phenyl)-5-(3-furanyl)benzimidazole (9h) was prepared analogously from 8h (Example 13). Purification was achieved by column-chromatography on silica gel using a mixture of dichloromethane and acetone (9:1) as the eluent. Yield: 32% (from 7h). Mp 183–184° C.

1-(3-(2-Methylimidazol-1-yl)phenyl)-5-(3-furanyl) benzimidazole (9j) was prepared analogously from 8j (Example 13). Purification was achieved by column-chromatography on silica gel using a mixture of ethyl acetate and methanol (9:1) as the eluent. Yield: 71%. Mp 105–107° C.

1-(3-(1-Pyrrolyl)phenyl)-5-(3-furanyl)benzimidazole (9k) was prepared analogously from 8k (Example 13). Purification was achieved by column-chromatography on silica gel using a mixture of ethyl acetate and petroleum ether (1:1) as the eluent. Yield: 42%. Mp 144–145° C.

1-(3-(2-Aminopyrimid-5-yl)phenyl)-5-(2-furanyl) benzimidazole (9l) was prepared analogously from 8l (Example 14). Purification was achieved by column-chromatography on silica gel using a mixture of ethyl acetate and methanol (9:1) as the eluent. Yield: 11%. Mp 220–222° C.

1-(3-(2-(Dimethylamino)pyrimid-5-yl)phenyl)-5-(2-furanyl)benzimidazole (9m) was prepared analogously from 8m (Example 13). Purification was achieved by column-chromatography on silica gel using a mixture of ethyl acetate and petroleum ether (1:1) as the eluent. Yield: 42% (from 7m). Mp 170–172° C.

1-(3-(1-Pyrrolyl)phenyl)-5-(2-furanyl)benzimidazole (9n) was prepared analogously from 8n (Example 13) and purified as described for 9m. Yield: 53%. Mp 137–139° C.

1-(3-(1-Imidazolyl)phenyl)-5-(2-furanyl)benzimidazole (9o) was prepared analogously from 8o (Example 13) and purified as described for 9c. Yield: 46%. Mp 175–177° C.

1-(3-(2-Aminopyrimid-5-yl)phenyl)-5-(3-furanyl) benzimidazole (9p) was prepared analogously from 8p (Example 14) and purified as described for 9l. Yield: 5%. Mp 222–223° C.

1-(3-(5-Pyrimidyl)phenyl)-5-iodobenzimidazole (11 b) was prepared analogously from 10b (Example 13). The crude product was used without further purification. Yield: 91%. Mp 197–199° C.

1-(3-(2-Methylthiazol-4-yl)phenyl)-5-iodobenzimidazole (11n) was prepared analogously from 10n (Example 13). Yield: 98%. Mp 163–164° C.

1-(3-(1-Pyrazolyl)phenyl)-5-iodobenzimidazole (11m) was prepared analogously from 10m (Example 13). Yield: 86%. Mp 209–211° C.

1-(3-(2-Pyridyl)phenyl)-5-iodobenzimidazole (11f) was prepared analogously from 10f (Example 13). Yield: 53% (from 6f). Mp 157–158° C.

1-(3-Bromophenyl)-5-(3-furanyl)benzimidazole in mixture with 1-(3-iodophenyl)-5-(3furanyl)benzimidazole (14q) was prepared analogously from 13q (Example 13). The crude product was used without purification (Example 12). Yield: 47%.

1-(4-(1-Imidazolyl)pyrimid-6-yl)-5-(3-furanyl) benzimidazole (18b) was prepared analogously from 17b (Example 26). Yield: 27% (from 16b). Mp 294–296° C.

1-(2-(1-Imidazolyl)pyridin-6-yl)-5-(3-furanyl) benzimidazole (18c) was prepared analogously from 17c (Example 26). The product was isolated by extraction and crystallization from ethyl acetate. Yield: 29%. Mp 170–173° C.

1-(3-(2-Thiazolyl)phenyl)-5-nitrobenzimidazole (21t) was prepared analogously from 20t (Example 13) in quantitative yield. Mp 251–260° C.

Example 16

1-(3-Nitrophenyl)pyrazol. A mixture of 1-iodo-3-nitrobenzene (18.7 g, 75 mmol), pyrazol (7.66 g, 113 mmol), potassium carbonate (11.2 g, 81 mmol) and catalytic amounts of cuprous iodide and copper-bronze in dry N-methyl-2-pyrrolidone (50 ml) is heated to 180° C. for 4.5 hours. After cooling the mixture is filtered through celite. The filtrate is poured into ice water (700 ml) and the product is filtered off, washed with water and dried to yield 13.57 g. Yield: 96%. Mp 85–87° C.

3-(1-Pyrazolyl)aniline (2m): A suspension of 3-(1-pyrazolyl)-1-nitrobenzene (5.5 g, 34.6 mmol) in conc. hydrochloric acid (50 ml) is heated to reflux. Stannous chloride dihydrat (24.2 g, 0.11 mol) is added portionwise and reflux is continued for half an hour. After cooling the precipitate is filtered off and dissolved in 200 ml water. The resulting solution is cooled in an ice-bath, rendered alkaline by addition of 12M aqueous sodium hydroxide and extracted with ethyl acetate. The extract is washed with brine, dried over sodium sulfate and evaporated to leave the product as a brownish oil. Yield: 3.9 g (71%).

1-(3-(2-Thiazolyl)phenyl-5-aminobenzimidazole (22t) was prepared analogously from 21t (Example 15). Isolated as an oil. Yield: 65%.

Example 17

3-(2-Methylthiazol-4-yl)aniline (2n): A mixture of 2-bromo-3'-nitroacetophenone (5 g, 20.5 mmol) and thioacetamide (1.4 g, 18.6 mmol). in glacial acetic acid (50 ml) is heated to reflux over night. After cooling the precipitate is filtered off, washed with water and dried to yield 2-methyl-4-(3-nitrophenyl)thiazole (3.47 g, 85%). Mp 87–88° C. This product is hydrogenated as described in Example 4 to yield 2n quantitatively. Mp 80–81° C.

Example 18

N-Acetyl 4-bromo-2-nitroaniline (1d): A solution of 4-bromoacetanilide (20 g, 93.4 mmol) in methanesulfonic acid is cooled to 10° C. Conc. nitric acid (12.6 ml) is added and the mixture is stirred at 40° C. for 2 hours. The mixture is poured into ice-water. The product is filtered off, washed with water and dried. Yield: 23.59 g (97%). Mp 99–100° C.

4-Bromo-2-nitroaniline (1f): A mixture of 1d (3.5 g, 13.5 mmol), dimethoxyethane (100 ml) and aqueous sodium hydroxide (50 ml, 1 M) is heated to 80° C. for 1 hour. After cooling the mixture is poured into ice-water. The product is filtered off, washed with water and dried. Yield 2.77 g (94%). Mp 109–110° C.

Example 19

N-Acetyl 4-(3-furanyl)-2-nitroaniline (1e): A mixture of 1d from Example 18 (8.5 g, 32.8 mmol), 3-furanylboronic acid (3.67 g, 32.8 mmol), sodium bicarbonate (13.8 g, 0.16 mol) and tetrakis(triphenylphosphine)palladium(0) (0.5 g) in a mixture of water (40 ml) and dimethoxyethane (80 ml) is heated to 80° C. under a stream of nitrogen over night. After cooling the mixture is poured into water and extracted with ethyl acetate. The organic phase is washed with brine, dried over sodium sulfate and concentrated under reduced pressure.(*). The residue is dissolved in 40 ml dimethoxyethane. Aqueous sodium hydroxide (78 ml, 1 M) is added and the mixture is stirred at ambient temperature over night. The mixture is poured into water and rendered acidic with diluted hydrochloric acid. The precipitate is filtered off, washed with water and dried to yield 1e (5.09 g, 76%). Mp 152–154° C.

1-(3-(2-Thiazolyl)phenyl)-5-(3-furanyl)benzimidazole (9t) was prepared analogously from 23t (Example 28) until (*). The residue was eluted through silica gel with a mixture of ethyl acetate and petroleum ether (1:1). Yield: 9%. Mp 102–105° C.

Example 20

N-(3-Bromophenyl)-4-(3-furanyl)-2-nitroaniline in mixture with N-(3-iodophenyl)-4-(3furanyl)-2-nitroaniline (12q): A mixture of 1-bromo-3-iodobenzene (2.65 ml, 20.8 mmol), 1e from Example 19 (4 g, 19.6 mmol), potassium carbonate (2.93 g, 21.2 mmol) and a catalytic amount of copper-bronze in dry N-methyl-2-pyrrolidone is heated to 180° C. over night. After cooling the mixture is poured into water. Ethyl acetate is added and the mixture is filtered through celite. The phases are separated and the aqueous phase is extracted twice with ethyl acetate. The combined organic extracts are dried over sodium sulfate and the solvent is removed under reduced pressure. The residue is purified by column-chromatography on silica gel using a mixture of ethyl acetate and petroleum ether (1:9) as the eluent. The product-mixture (12q) is isolated as a red oil (1.44 g) which is used directly in the next step (see Example 13).

Example 21

N-(3-Carboxyphenyl)-4-(3-furanyl)-2-nitroaniline (12r): A mixture of 1e from Example 19 (5 g, 24.5 mmol), 3-iodobenzoic acid (6.69 g, 27 mmol), potassium carbonate (3.79 g, 27.5 mmol) and a catalytic amount of copper-bronze in 30 ml dry N-methyl-2-pyrrolidone is heated to 180° C. overnight. After cooling water is added and the mixture is washed twice with ethyl acetate. The aqueous phase is rendered acidic with diluted hydrochloric acid and the oily precipitate is filtered off. This precipitate is extracted with ethyl acetate, and the extract is purified by column-chromatography on silica gel using a mixture of ethyl acetate and petroleum ether (1:1) as the eluent. Yield: 2.56 g (32%). Mp 203–205° C.

Example 22

1-(3-Carboxyphenyl)-5-(3-furanyl)benzimidazole (14r): To 13r from Example 4 (2.4 g, 8.16 mmol) is added formic acid (25 ml) and the mixture is stirred at 80° C. for 1.5 hours. After cooling the mixture is poured into ice-water. The precipitate is filtered off, washed with methanol and dried to yield 14r (0.89 g, 40%). Mp 272–274° C.

1-(-3-(3-(2-Pyridyl)oxadiazol-5-yl)phenyl)-5-(3-furanyl) benzimidazole (9r): A solution of 14r (0.43 g, 1.41 mmol) in dry THF (10 ml) is heated to reflux under nitrogen. Carbonyldiimidazole (0.4 g, 2.48 mmol) is added and reflux is continued for 3 hours. 2-(Oximimido)pyridine (0.48 g, 3.54 mmol) is added and the resulting mixture is refluxed over night. After cooling the solvent is removed by evaporation and the residue is partitioned between water and ethyl acetate. The organic phase is dried over sodium sulfate and evaporated to dryness. The residue is dissolved in toluene (15 ml), a catalytic amount of pTSA is added and the mixture is refluxed over night. The solvent is evaporated under reduced pressure and the residue is purified by column-chromatography on silica gel using a mixture of ethyl acetate and petroleum ether (1:1) as the eluent. Yield of 9r: 0.16 g (28%). Mp 183–186° C.

1-(3-(3-Cyclopropyloxadiazol-5-yl)phenyl)-5-(3-furanyl) benzimidazole (9s) was prepared analogously from 14r and cyclopropyloximimide. Yield: 19%. Mp 144–146° C.

Example 23

2-Chloro-6-(1-imidazolyl)pyridine (15a): A mixture of 2,6-dichloropyridine (5 g, 33.78 mmol), imidazole (2.3 g, 33.78 mmol) and potassium carbonate (4.66 g, 33.78 mmol) in DMF (50 ml) is heated to 85° C. over night. The cooled mixture is poured into ice-water and unreacted starting material is filtered off. The filtrate is acidified with diluted hydrochloric acid and is extracted once with ethyl acetate. The aqueous phase is rendered alkaline by addition of aqueous sodium hydroxide (10 M) and extracted with ethyl acetate. The organic extract is dried over sodium sulfate, concentrated under reduced pressure and eluted through silica gel with a mixture of ethyl acetate and methanol (9:1). Evaporation of solvent leaves 15a. Yield: 2.37 g (39%). Mp 71–73° C.

Example 24

4-Chloro-6-(1-imidazolyl)pyrimidine (15b): A mixture of 4,6-dichloropyrimidine (5 g, 33.56 mmol), imidazole (2.28 g, 33.56 mmol) and potassium carbonate (4.63 g, 33.56 mmol) in DMF (50 ml) is stirred at room temperature over night. The mixture is diluted with four volumes of water and extracted with dichloromethane. The organic extract is concentrated under reduced pressure and eluted through silica gel with a mixture of ethyl acetate and methanol (9:1). Evaporation of solvent and trituration of the residue with a mixture of diethyl ether and petroleum ether (1:1) leaves 15b (4.07 g, 67%). Mp 198–200° C.

Example 25

N-(2-(1-Imidazolyl)pyridin-6-yl)-4-bromo-2-nitroaniline (16a): To a solution of if from Example 18 (2.7 g, 12.5 mmol) in dry DMF (25 ml) is added sodium hydride (0.5 g of a 60% dispersion in mineral oil) and the mixture is stirred for 30 min. 15a (Example 23) (2.25 g, 12.5 mmol) is added and the mixture is heated to 100° C. over night. After cooling the mixture is poured into ice-water. The precipitate is filtered off, dried and redissolved in ethyl acetate. The filtrate is extracted with ethyl acetate. The combined product solutions are concentrated and purified by column-chromatography on silica gel using a mixture of ethyl acetate and methanol (9:1) as the eluent. Evaporation of solvent and trituration of the residue with a mixture of petroleum ether and diethyl ether (1:1) affords 16a (0.93 g, 21%). Mp 194–195° C.

N-(4-(1-Imidazolyl)pyrimid-6-yl)-4-(3-furanyl)2-nitroaniline (16b) was prepared analogously from 15b (Example 24) and 1e (Example 19). Ethyl acetate was used as the eluent for the chromatographic workup. Yield: 23%. Mp 198–200° C.

Example 26

N-(4-(1-Imidazolyl)pyrimid-6-yl)-2-amino-4-(3-furanyl) aniline (17b) A suspension of 16b (Example 25) (0.38 g, 1.1 mmol) in a mixture of ethanol and dichloromethane is hydrogenated at ambient temperature using Raney Nickel (50% slurry in water) as the catalyst. When the hydrogen uptake has ceased the mixture is filtered through celite and the filtrate is evaporated to leave 17b as an oil which is used without purification.

N-(2-(1-Imidazolyl)pyrid-6-yl)-2-amino-4-(3-furanyl) aniline (17c) A suspension of 16c from Example 12 (0.9 g, 2.6 mmol) in 50 ml a mixture of ethanol and dichloromethane (4:1) is added Pd catalyst (0.15 g, 5% on activated carbon) and hydrogenated at ambient temperature until the hydrogen uptake has ceased. The mixture is filtered through celite and the filtrate is evaporated to leave 17c as an oil which is used without purification.

Example 27

N-(3-(2-Thiazolyl)phenyl)-2,4-dinitroaniline (19t): A mixture of 2,4-dinitrofluorobenzene (1.14 ml, 9.1 mmol), 2t from Example 2 (1.6 g, 9.1 mmol) and potassium carbonate (1.51 g, 10.9 mmol) in dry N-methyl-2-pyrrolidone (10 ml) is heated to 80° C. for 2 hours. The cooled mixture is poured into ice-water. The precipitate is filtered off, washed with water and dried to yield: 3.05 g (98%). Mp 1 97–203° C.

Example 28

1-(3-(2-Thiazolyl)phenyl)-5-iodobenzimidazole (23t): A suspension of 22t from Example 16 (0.85 g, 2.91 mmol) in hydrochloric acid is cooled to −5° C. A solution of sodium nitrite (0.22 g, 3.2 mmol) in 3 ml water is added dropwise keeping the temperature below 0° C. Following the addition the mixture is stirred at (−5) −0° C. for 20 min. A solution of potassium iodide (0.6 g, 3.64 mmol) in 3 ml water is added and the mixture is stirred at ambient temperature over night. To the reaction mixture is added aqueous sodium sulfite until the iodine color has disappeared. The resulting mixture is extracted with ethyl acetate. The organic phase is washed with aqueous sodium carbonate, dried over sodium sulfate and filtered through silica gel. The filtrate is evaporated to dryness to yield 23t. Yield: 23%. Melts with decomposition from 175° C.

Eksempel 29

N-(3-Iodophenyl)-4-cyano-2-nitroaniline (29): To a solution of 4-chloro-3-nitrobenzonitril (1.82 g, 10 mmol) in dry DMF (25 ml) is added triethylamine (1.54 ml, 11 mmol) and 3-iodoaniline (1.2 ml, 10 mmol) and the mixture is heated to 80–100° C. over night. After cooling the mixture is poured into four volumes of ice-water. The precipitate is filtered off, washed with water and dried. This crude product is washed with hot ethanol to yield 2.1 g (58%) of the title compound. Mp. 211–212° C.

Example 30

2-amino-(N-(3-iodophenyl))-4-cyanoaniline (30): To a suspension of (29): (2.1 g, 5.75 mmol) in methanol (50 ml) is added ammonium chloride (0.92 g, 17.25 mmol) and sodium sulfide nonahydrate (4.14 g, 17.25 mmol) and the mixture is heated to reflux for 1.5 hours. After cooling the mixture is poured into ice-water (200 ml) and the product is filtered off, washed with water and dried to leave 1.8 g (93%) of the title compound. Mp. 170–172° C.

Example 31

5-cyano-1-(3-iodophenyl)benzimidazole (31): A suspension of (30) (1.8 g, 5.36 mmol) in formic acid (20 ml) is heated to 80–100° C. for 1.5 hours. The hot reaction mixture is filtered through a cotton pad into ice-water (100 ml). The precipitate is filtered off, washed with water and dried. This crude product is dissolved in dichloromethane and is brought to precipitation by addition of petroleum ether. The product is filtered off and dried. Yield: 1.38 g (75%) of the title compound. Mp. 177–179° C.

Example 32

5-cyano-1-(3-(3-pyridyl)phenyl)benzimidazol (32a): A mixture of (31) (4 g, 11.6 mmol), diethyl 3-pyridylborane (2.04 g, 13.9 mmol), potassium carbonate (4.8 g, 34.8 mmol) and tetrakis(triphenylphosphine)palladium(0) (0.2 g) in a mixture of water (20 ml) and dimethoxyethane is stirred at 80° C. in a nitrogen atmosphere overnight. After cooling the resulting suspension is poured into water and the crude product is filtered off, washed with water and dried. Purification is achieved by column-chromatography on silica gel using a mixture of ethyl acetete and methanol (9:1) as the eluent. Yield 2.46 g (72%) of the title compound. Mp.191–193° C.

5-cyano-1-(3-(1-imidazolyl)phenyl)benzimidazol (32b) was prepared analogously.

Example 33

2-Tributylstannyl(thiazole) (33):To a solution of thiazol (0.71 ml, 10 mmol) in dry THF (20 ml) was added dropwise 1.6 M-BuLi in hexane (6.9 ml, 11 mmol) under argon at −78° C. The reaction mixture was stirred at −78° C. for 0.5 hr and $Bu_3SnCl$ (3.1 ml, 11 mmol) was added dropwise. After stirring for 1 hr at −78° C. and for 1 hr at room temperature, the mixture was concentrated, triturated with water (50 ml) and extracted with diethylether (100 ml×3). The extract was washed with brine, dried and concentrated under reduced pressure to give (33) as colorless oil.(3.7 g, quant.).

Example 34

5-Acetyl-1-(3-(2-thiazolyl)phenyl)benzimidazole (34): To a solution of (33) (3.6 g, 9.7 mmol) in dry THF (20 ml) was added 5-acetyl-1-(3-bromophenyl)benzimidazole (1.5 g, 4.8 mmol) and $(PPh_3)_2PdCl_2$ (340 mg, 0.48 mmol) under argon. The reaction mixture was stirred at 80° C. for 24 hr in a 50 ml sealed tube. After cooling the mixture was concentrated, triturated with water (100 ml) and extracted with $CH_2Cl_2$ (200 ml×3). The extract was washed with brine, dried and concentrated under reduced pressure. The residue was washed with ether to afford crystaline (34) (1.5 g, 89%).

5-Acetyl-1-(3-bromophenyl)benzimidazole was prepared as follows:

4-Acetyl-2-nitroaniline: N-(4-acetyl-2-nitrophenyl) acetamide (26.5 g, 11.94 mmol) was added to a mixture of water and concentrated sulfuric acid, 150 ml (1:2). After 15 minutes the mixture was poured into water. The product was filtered off, washed with water and dried.

N-(3-bromophenyl)-4-acetyl-2-nitroaniline: A mixture of 4-acetyl-2-nitroaniline (3.41 g, 18.94 mmol), 1,3-dibromobenzene (4.6 ml, 38.06 mmol), potassium carbonate (2.62 g, 19 mmol) and a catalytic amount of copper bronze is heated with stirring to 180° C. under a stream of nitrogen for 2 days. After cooling the solid reaction cake is extracted with a mixture of dichloromethane and methanol (9:1). The extract is concentrated under reduced pressure. The residue is extracted with ethyl acetate. This extract is concentrated under reduced pressure and the residue is eluted through silica gel with a mixture of petroleum ether and ethyl acetate (4:1) to afford the pure product. Yield 0.67 g (10.6%). M.p. 142–144° C.

5-Acetyl-1-(3-bromophenyl)benzimidazole: N-(3-bromophenyl)-4-acetyl-2-nitroaniline (9.0 g, 26,63 mmol) was suspended in 99% ethanol (100 ml). Raney nickel was added and the mixture was hydrogenated at ambient pressure for 20 hours. Chloroform was added. The mixture was filtered through celite and evaporated in vacuo to afford 8.03 g oil. To this oil 80 ml formic acid was added and the mixture was heated to 80° C. for 1.5 hours. Excess formic acid was removed in vacuo. The residue was stirred in water and and rendered alkaline with aqueous sodium hydroxide. The product was filtered off washed with water and dried.

Example 35

5-Cyano-1-(3-(2-thiazolyl)phenyl)benzimidazole (35): 5-cyano-1-(3-(2thiazolyl)phenyl)benzimidazole was synthesized as described in Example 34 by using (31) (2.0 g, 5.9 mmol) instead of 5-acetyl-1-(3-bromophenyl) benzimidazole, $(PPh_3)_2PdCl_2$ (100 mg, 0.14 mmol) and 2-(tributylstannyl)thiazole (3.6 g, 9.7 mmol). The reaction gave 5-cyano-1-(3-(2-thiazolyl)phenyl)benzimidazole (1.5 g, 86%).

Example 36

4-(3-Nitrophenyl)pyrimidine (36): A mixture of 4-phenylpyrimidine (10 g, 64 mmol) and conc. $H_2SO_4$ (33 ml) was added to a mixture of conc. $H_2SO_4$ (22 ml) and conc. $HNO_3$ (16 ml) at 0° C. The resulting mixture was stirred at 0° C. for 2 hr, poured onto crushed ice, and extracted with $CH_2Cl_2$. The extract was washed with a 5% aqueous $NaHCO_3$ solution, dried over $MgSO_4$ and concentrated under reduced pressure. The residue was triturated with isopropanol and the precipitate was filtered off and dried under reduced pressure to give (36) (6.4 g, 50%).

Example 37

4-(3-Aminophenyl)pyrimidine (37):To a suspension of (36) (6.3 g, 31 mmol) in a mixture of MeOH (60 ml) and THF (30 ml) was added 5% palladium on activated carbon (300 mg) and the mixture was hydrogenated at ambient pressure for 1 hr. The mixture was filtered and concentrated under reduced pressure. The residue was purified by column-chromatography on silica gel using a mixture of hexane and ethylcetate (3:1) as the eluent to give (37) (5.1 g, 96%).

Example 38

N-(3-(4-Pyrimidyl)phenyl)-4-cyano-2-nitroaniline (38): To a mixture of (37) (5.5 g, 30 mmol) and 4-chloro-3-nitrobenzonitril (5.1 g, 30 mmol) in THF (120 ml) was added sodium hydride (2.3 g, 50% suspension in mineral oil). After stirring at room temperature for 2 days, the mixture was poured into water and extracted with $CH_2Cl_2$. The extract was concentrated under reduced pressure and the residue was triturated with diethyl ether to yield crystalline (38) (9.2 g, 96%).

Example 39

N-(3-(4-pyrimidyl)phenyl)-4-cyano-2-aminoaniline (39): was synthesized as described in example 37 using (38) (9.2 g, 29 mmol) instead of 4-(3-nitrophenyl)pyrimidine and 600 g catalyst. The reaction gave (39) (8.3 g, quant.)

Example 40

5-Cyano-1-(3-(4-pyrimidinyl)phenyl)benzimidazole (40): A mixture of (39) (3.0 g, 10 mmol) and $HCO_2H$ (20 ml) was stirred at 110° C. for 1 hr. The mixture was concentrated in vacuo. The residue was partitioned between a 5% aqueous $NaHCO_3$ solution and $CH_2Cl_2$. The organic phase was dried over $MgSO_4$ and the solvent was removed by evaporation. The residue was triturated with ethyl acetate to afford crystalline (40). (2.6 g, 85%).

Example 41

5-Formyl-1-(3-(4-pyrimidinyl)phenyl)benzimidazole (41 a): Raney Ni (2.2 g) was added to a solution of (40) (3.9 g) in a mixture of $HCO_2H$ (48 ml) and water (18 ml). The mixture was stirred under argon at 100° C. for 0.5 hours. After cooling the mixture was filtered. The filtrate was concentrated partitioned between 1 M $NaHCO_2$ solution and ethyl acetate. The ethyl acetate extract was washed with brine, dried and concentrated under reduced pressure to give (41a) (2.7 g, 69%).

5-Formyl-1-(3-(2-thiazolyl)-phenyl)benzimidazole (41 b) was prepared analogously from (35), 5-Formyl-1-(3-(1-imidazolyl)-phenyl)benzimidazole (41c) was prepared analogously from (32b), and 5-Formyl-1-(3-(3-pyridyl)-phenyl)benzimidazole (41d) was prepared analogously from (32a).

Example 42

5-Formyl-1-(3-(4-pyrimidinyl)phenyl)benzimidazole oxime (42a): 41a (2.7 g) was added to a mixture of ethanol (100 ml), $NH_2OH,HCl$ (1.9 g, 3 equivalents) and triethylamine (1.3 ml, 1 equivalent) and the mixture was stirred at 60° C. for one hour. The mixture was chilled to 0° C. and the precipitate was filtered off, washed with water, and dried under reduced pressure to give (42a) (2.2 g, 77%).

5-Formyl-1-(3-(2-thiazolyl)-phenyl)benzimidazole oxime (42b) was prepared analogously from (41 b), 5-Formyl-1-(3-(1-imidazolyl)-phenyl)benzimidazole oxime (42c) was prepared analogously from (41c), and 5-Formyl-1-(3-(3-pyridyl)-phenyl)benzimidazole oxime (42d) was prepared analogously from (41d).

Example 43

5-(3-Isoxazolyl)-1-(3-(4-pyrimidinyl)phenyl) benzimidazole (43a): A mixture of 42a (2.1 g) and N-chlorsuccinimide (1.1 g, 1.2 equivalents) in DMF (100 ml) was stirred under argon at 60° C. for 0.5 hours. Vinyl bromide (25 ml) was added to the reaction mixture under ice-cooling, and thereafter triethylamine (4.8 ml, 5 equivalents) in 15 ml DMF was added dropwise over one hour. The mixture was stirred at 0° C. for 3 hours and at room temperature overnight. The mixture was poured into water and extracted with ethyl acetate. The organic phase was washed with brine, dried, and concentrated under reduced pressure. The residue was purified by column-chromatography on silica gel using a mixture of $CH_2Cl_2$ and methanol (30:1) as the eluent to give 5-(3-isoxazolyl)-1-(3-(4-pyrimidinyl)phenyl)benzimidazole (1.5 g, 64%).M.p. 214–215° C.

5-(3-Isoxazolyl)-1-(3-(2-thiazolyl)phenyl)benzimidazole (43b) M.p. 157–158° C. was prepared analogously from (42b)

5-(3-isoxazolyl)-1-(3-(1-imidazolyl)phenyl) benzimidazole (43c) was prepared analogously from (42c), M.p. 230–234° C.

5-(3-isoxazolyl)-1-(3-(3-pyridyl)phenyl)benzimidazole (43d) was prepared analogously from (42d) M.p. 208–210° C.

Example 44

5-acetyl-1-(3-(3-pyridyl)phenyl)benzimidazole (44a): 4-Fluoro-3-nitroacetophenone: Concentrated sulphuric acid (200 ml) is cooled to 5° C. 4-Fluoroacetophenone (20 ml, 164.76 mmol) is added so that the temperature does not rise above 10° C. The mixture is cooled to 0–5° C. and potassium nitrate (25 g, 247.14 mmol) is added portionwise over 2 hours keeping the temperature at 0–5° C. Following the addition the mixture is stirred at this temperature for 2 hours. The mixture is poured on ice (600 g) and the crude product is filtered off. Column-chromatographic purification on silica-gel using a mixture of ethylacetate and petroleum ether (1:9) as the eluent affords 18.19 g pure 4-fluoro-3-nitroacetophenone (60%).

3-(3-Pyridyl)nitrobenzene: To 3-bromopyridine (8.53 g, 54 mmol) in ethyleneglycol dimethylether (180 ml) is added 3-nitrophenylboronic acid (10 g, 59.95 mmol), aqueous potassium carbonate (90 ml, 2M) and tetrakis (triphenylphosphine)palladium (0.5 g, 0.43 mmol). The mixture is refluxed gently in a nitrogen atmosphere overnight. The cooled reaction mixture is filtered and water (600 ml) is added to the filtrate. The precipitate is filtered off and washed with water. This crude product is dissolved in hot water (400 ml) with addition of hydrochloric acid (25 ml, 4 M). The mixture is filtered while still hot. The filtrate is cooled in an ice bath and pure 3-(3-pyridyl)-nitrobenzene is precipitated by addition of 12 M NaOH. Yield 9.14 g (85%).

3-(3-Pyridyl)aniline: 3-(3-pyridyl)-nitrobenzene (9.1 g, 45.5 mmol) in ethanol (125 ml) is hydrogenated at ambient pressure for 1.75 hours using Raney Nickel as the catalyst. Filtration of the resulting solution through celite followed by evaporation of solvent quantitatively yields 3-(3-pyridyl) aniline.

4-Acetyl-2-nitro-N-(3-(3-pyridyl)phenyl)aniline: A mixture of 4-Fluoro-3-nitroacetophenone (5 g, 27.3 mmol) and 3-(3-pyridyl)aniline (4.62 g, 27.2 mmol) in dry 1-methyl-2-pyrrolidone (10 ml) is stirred at 40–50° C. overnight. The resulting solid reaction mixture is suspended in ice water (50 ml) and made alkaline by addition of 1 M $NaHCO_3$. The product is filtered off, washed with water and dried to yield 7.68 g 4-acetyl-2-nitro-N-(3-(3-pyridyl)phenyl)aniline (85%).

5-Acetyl-2-(3-(3-pyridyl)phenylamino)aniline: 4-acetyl-2-nitro-N-(3-(3-pyridyl)-phenyl)-aniline (2 g, 6 mmol) is suspended in a mixture of ethanol (50 ml) and dichloromethane (10 ml) and is hydrogenated at ambient pressure using palladium (5% on activated carbon) as the catalyst. Filtration of the resulting solution through celite followed by evaporation of solvent leaves an oil which upon trituration with a mixture of diethylether and petroleumether (1:1) affords 1.46 g pure 5-acetyl-2-(3-(3-pyridyl)phenylamino) aniline (80%).

5-Acetyl-1-(3-(3-pyridyl)phenyl)benzimidazole: 5-acetyl-2-(3-(3-pyridyl)phenylamino)aniline (5 g, 16.5 mmol) in formic acid (50 ml) is stirred at 90° C. for 1.5 hours. The cooled reaction mixture is made alkaline by addition of 12 M NaOH. 5-acetyl-1-(3-(3-pyridyl)phenyl) benzimidazole is filtered off washed with water and dried. Quantitative yield. m.p. 195–97° C.

The following compound was prepared analogously:

5-Acetyl-1-(3-(4-pyrimidinyl)phenyl)benzimidazole (44b).

Example 45

5-(5-Isoxazolyl)-1-(3-(4-pyrimidinyl)phenyl) benzimidazole (45a) was prepared as follows: 5-(3-dimethylamino-1-oxo-2-propen-1-yl)-1-(3-(4-pyrimidinyl) phenyl)benzimidazole: (44b) (314 mg) was reacted with DMF-dimethylacetal (1.5 ml) under argon in DMF (3 ml) at 120° C. for 5 hours. After cooling to the mixture was poured into water and extracted with ethyl acetate. The organic phase was washed with brine, dried, and concentrated under reduced pressure. The residue was purified by column-chromatography on silica gel using a mixture of $CH_2Cl_2$ and methanol (30:1) as the eluent to give 5-(3-dimethylamino-1-oxo-2-propen-1-yl)-1-(3-(4pyrimidinyl)phenyl) benzimidazole (320 mg, 87%).

5-(5-lsoxazolyl)-1-(3-(4-pyrimidinyl)phenyl) benzimidazole: A mixture of 5-(3dimethylamino-1-oxo-2-propen-1-yl)-1-(3-(4-pyrimidinyl)phenyl)benzimidazole (307 mg) and $NH_2OH,HCl$ (135 mg, 2.5 equivalents) in methanol (14 ml) was stirred at 80° C. for 2 hours. After cooling the mixture was poured into water and extracted with ethyl acetate. The organic phase was washed with brine, dried, and concentrated under reduced pressure. The residue was chromatographied ($CH_2Cl_2$-methanol 40:1 (v/v)) to give 5-(5-isoxazolyl)-1-(3-(4-pyrimidinyl)phenyl) benzimidazole (226 mg, 80%).

The following compounds was prepared analogously:

5-(5-isoxazolyl)-1-(3-(2-thiazolyl)phenyl)benzimidazole (45b) was prepared analogously from (34), M.p. 186–188° C.

5-(5-isoxazolyl)-1-(3-(3-pyridyl)phenyl)benzimidazole (45c) was prepared analogously from (44a) M.p. 218–219° C. The compounds prepared in the above examples are listed in the following tables 1 and 2.

TABLE 1

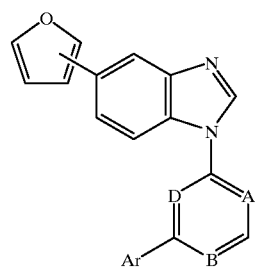

| Compound No. | Ar | D | A | B | Furan subst. site | m.p. (° C.) | Ex. |
|---|---|---|---|---|---|---|---|
| 9c | 1-imidazolyl | CH | CH | CH | 3 | 203–204 | 15 |
| 9h | 2-(dimethylamino)-5-pyrimidyl | CH | CH | CH | 3 | 183–184 | 15 |
| 9j | 2-methyl-1-imidazolyl | CH | CH | CH | 3 | 105–107 | 15 |
| 9k | 1-pyrrolyl | CH | CH | CH | 3 | 144–145 | 15 |
| 9l | 2-amino-5-pyrimidyl | CH | CH | CH | 2 | 220–222 | 15 |
| 9m | 2-(dimethylamino)-5-pyrimidyl | CH | CH | CH | 2 | 170–172 | 15 |
| 9n | 1-pyrrolyl | CH | CH | CH | 2 | 137–139 | 15 |

TABLE 1-continued

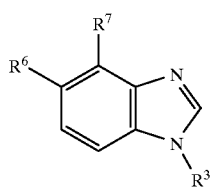

| Compound No. | Ar | D | A | B | Furan subst. site | m.p. (° C.) | Ex. |
|---|---|---|---|---|---|---|---|
| 9o | 1-imidazolyl | CH | CH | CH | 2 | 175–177 | 15 |
| 9p | 2-amino-5-pyrimidyl | CH | CH | CH | 3 | 222–223 | 15 |
| 9b | 5-pyrimidyl | CH | CH | CH | 3 | 216–218 | 12 |
| 9N | 2-methyl-4-thiazolyl | CH | CH | CH | 3 | 136–138 | 12 |
| 9M | 1-pyrazolyl | CH | CH | CH | 3 | 170–173 | 12 |
| 9f | 2-pyridyl | CH | CH | CH | 2 | 135–136 | 12 |
| 9q | 3-furanyl | CH | CH | CH | 3 | 149–150 | 12 |
| 9r | 3-(2-pyridyl)-oxadiazol-5-yl | CH | CH | CH | 3 | 183–186 | 22 |
| 9s | 3-cyclopropyl oxadiazol-5-yl | CH | CH | CH | 3 | 144–146 | 22 |
| 9t | 2-thiazolyl | CH | CH | CH | 3 | 102–105 | 19 |
| 18b | 1-imidazolyl | CH | N | N | 3 | 294–296 | 15 |
| 18c | 1-imidazolyl | N | CH | CH | 3 | 170–173 | 15 |

TABLE 2

| Ar | Isoxazol subst. site | m.p. (°C.) | example |
|---|---|---|---|
| 4-pyrimidyl | 3 | 214–215 | 43 |
| 3-pyridyl | 3 | 208–210 | 43 |
| 2-thiazolyl | 3 | 157–158 | 43 |
| 1-imidazolyl | 3 | 230–234 | 43 |
| 2-thiazolyl | 5 | 186–188 | 45 |
| 3-pyridyl | 5 | 218–219 | 45 |

We claim:

1. A compound having the formula:

or a pharmaceutically acceptable salt thereof, or a racemic mixture thereof, or an optical isomer thereof, or an oxide thereof wherein $R^3$ is

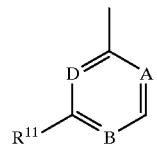

wherein

A, B and D are each CH, or N and $R^{11}$ is phenyl, benzimidazolyl, or monocyclic heteroaryl, all of which is optionally substituted one or more times with substituents selected from the group consisting of alkyl, alkoxy, phenyl, halogen, $CF_3$, amino, nitro, cyano, acyl, acylamino, phenyl and monocyclic heteroaryl; and one of $R^6$ and $R^7$ is hydrogen and the other is furanyl or isoxazolyl each of which is optionally substituted one or more times with substituents selected from the group consisting of halogen, alkyl, alkoxy and phenyl, with the proviso that $R^{11}$ is not 3-pyridyl.

2. A compound of claim 1, which is 1-(3-(1-Imidazolyl)phenyl)-5-(3-furanyl)benzimidazole; 1-(3-(2-methyl-1-imidazolyl)phenyl)-5-(3-furanyl)benzimidazole; or 1-(3-(5-pyrimidinyl)phenyl)-5-(3-furanyl)benzimidazole; or a pharmaceutically acceptable salt thereof or an oxide thereof.

3. A compound of claim 1, which is 1-(3-(2-(Dimethylamino)pyrimid-5-yl)phenyl)-5-(3-furanyl)benzimidazole; 1-(3-(1-Pyrrolyl)phenyl)-5-(3-furanyl)benzimidazole; 1-(3-(2-Aminopyrimid-5-yl)phenyl)-5-(2-furanyl)benzimidazole; 1-(3-(2-Dimethylamino)pyrimid-5-yl)phenyl)-5-(2-furanyl)benzimidazole; 1-(3-(1-Pyrrolyl)phenyl-5-(2-furanyl)benzimidazole; 1-(3-(1-Imidazolyl)phenyl)-5-(2-furanyl)benzimidazole; 1-(3-(2Aminopyrimid-5-yl)phenyl)-5-(3-furanyl)benzimidazole; 1-(4-(1-Imidazolyl)pyrimid-6-yl)-5-(3-furanyl)benzimidazole; 1-(2-(1-Imidazolyl)pyridin-6-yl)-5-(3-furanyl)benzimidazole; 1-(3-(2-Thiazolyl)phenyl)-5-(3-furanyl)benzimidazole; 1-(3-(2Methylthiazol-4-yl)phenyl)-5-(3-furanyl)benzimidazole; 1-(3-(1Pyrazolyl)phenyl)-5-(3-furanyl)benzimidazole; 1-(3-(2-Pyridyl)phenyl)-5-(2-furanyl)benzimidazole; 1-(3-(3-Furanyl)phenyl-5-(3-furanyl)benzimidazole; 1-(3-(3-(2Pyridyl)-1,2,4-oxadiazol-5-yl)phenyl)-5-(3-furanyl)benzimidazole; 1-(3-(3-Cyclopropyl-1,2,4-oxadiazol-5-yl)phenyl)-5-(3-furanyl)benzimidazole; 5-(3-Isoxazolyl)-1-(3-(4-pyrimidinyl)phenyl)benzimidazole; 5-(3-Isoxazolyl)-1-(3-(2-thiazolyl)phenyl)benzimidazole; 5-(3-isoxazolyl)-1-(3-(1-imidazolyl)phenyl)benzimidazole; 5-(5-Isoxazolyl)-1-(3-(4-pyrimidinyl)phenyl)benzimidazole; or 5-(5-isoxazolyl)-1-(3-(2-thiazolyl)phenyl)benzimidazole; or a pharmaceutically acceptable salt thereof or an oxide thereof.

4. A pharmaceutical composition comprising an effective amount of a compound of any of claims 1–3, or a pharmaceutically-acceptable addition salt thereof or an oxide thereof, together with at least one pharmaceutically-acceptable carrier or diluent.

5. A method of treating a disorder or disease of a living animal body, which disorder or disease is responsive to modulation of the $GABA_A$ receptor complex of the central nervous system comprising administering to such a living animal body in need thereof a therapeutically-effective amount of a compound of any of claims 1–3.

6. The method of claim 5, wherein a disorder or disease responsive to the positive modulation of the $GABA_A$ receptor complex is treated.

7. The method of claim 5, wherein said disease is selected from the group consisting of anxiety, sleep disorders, memory disorders and epilepsy.

8. The method of claim 5, wherein the active ingredient is administered in the form of a pharmaceutical composition thereof, in which it is present together with a pharmaceutically-acceptable carrier or diluent.

9. A method of modulating a $GABA_A$ receptor complex comprising exposing said receptor complex to an effective amount of a compound of any of claims 1–3.

10. The pharmaceutical composition of claim 4, wherein the compound is present in 0.1–100 mg/unit dosage.

11. The method of claim 5, wherein said disease is a convulsive disorder.

12. The method of claim 5, wherein said living animal body is a human.

13. A method of making a compound of claim 1, comprising using a sythesis scheme selected from the following schemes a–f:

a)

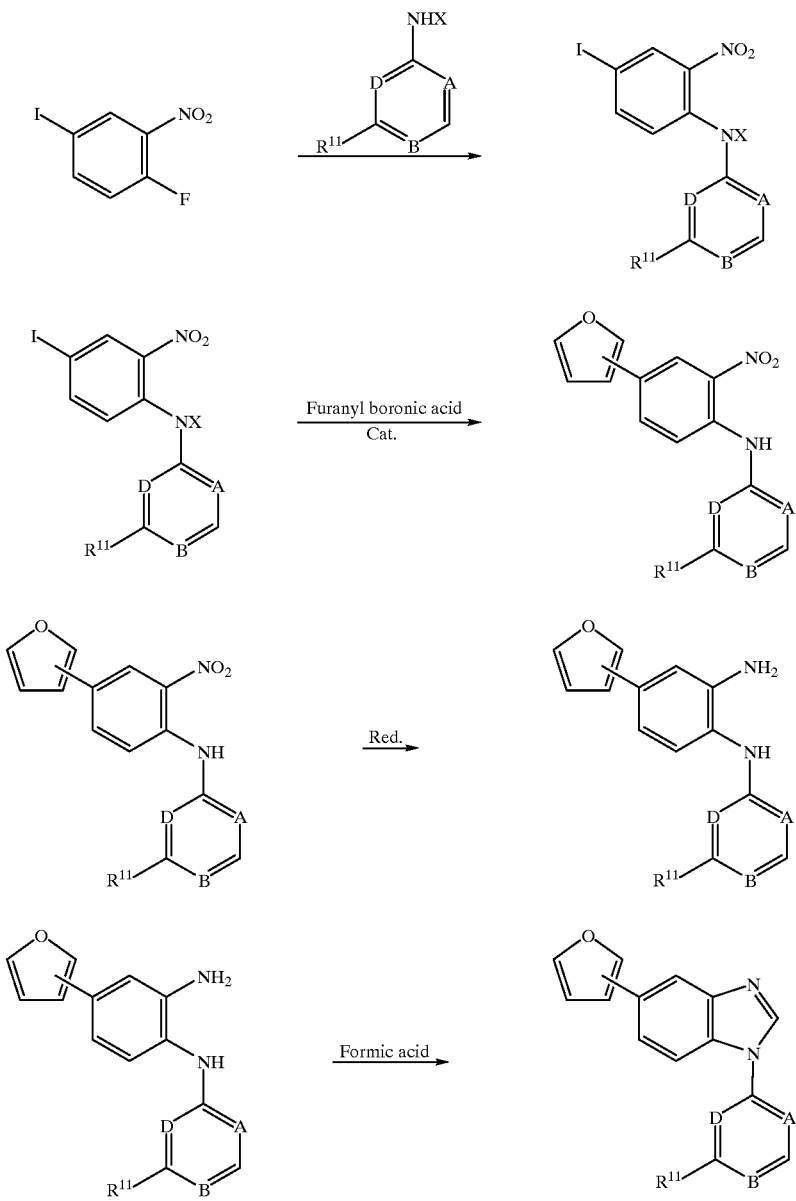

b)

-continued
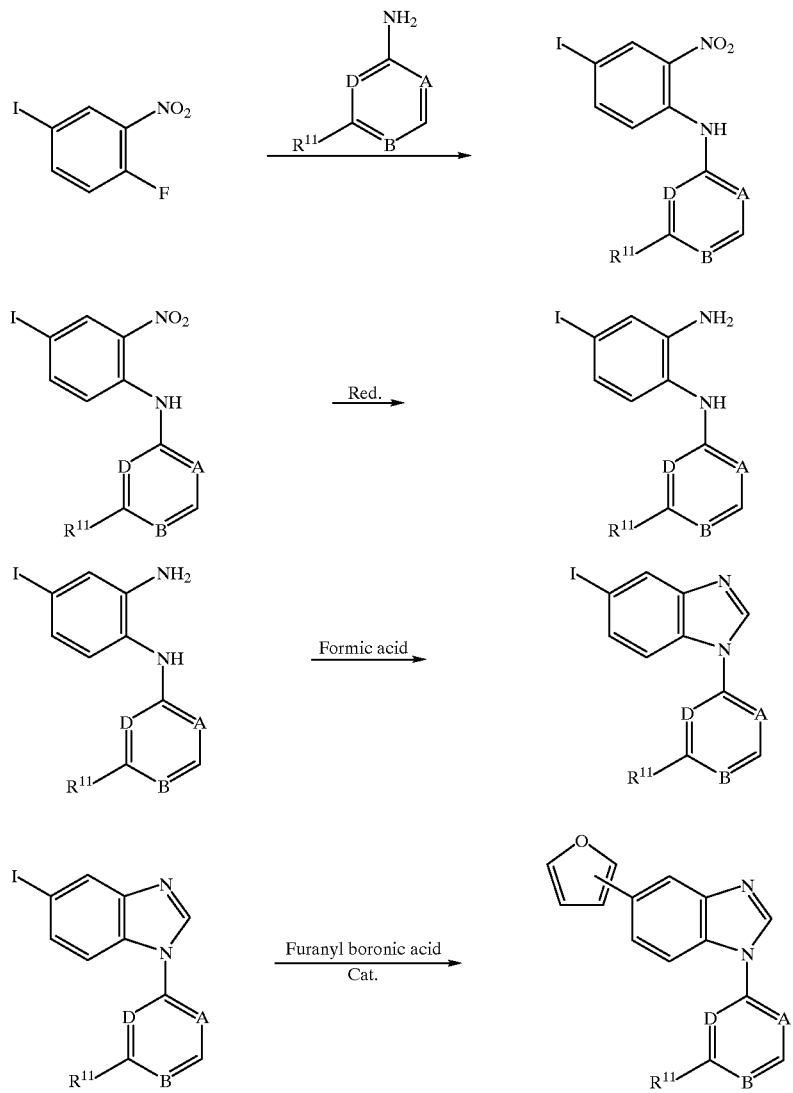
c)
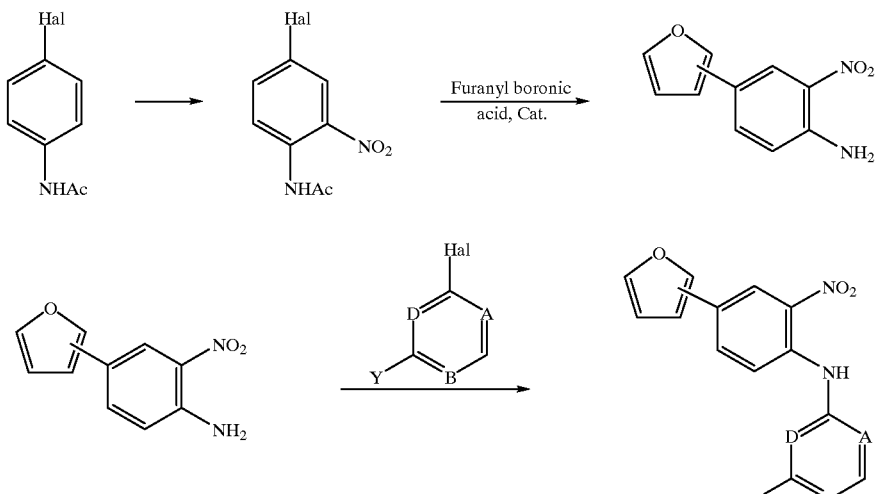

31    -continued    32
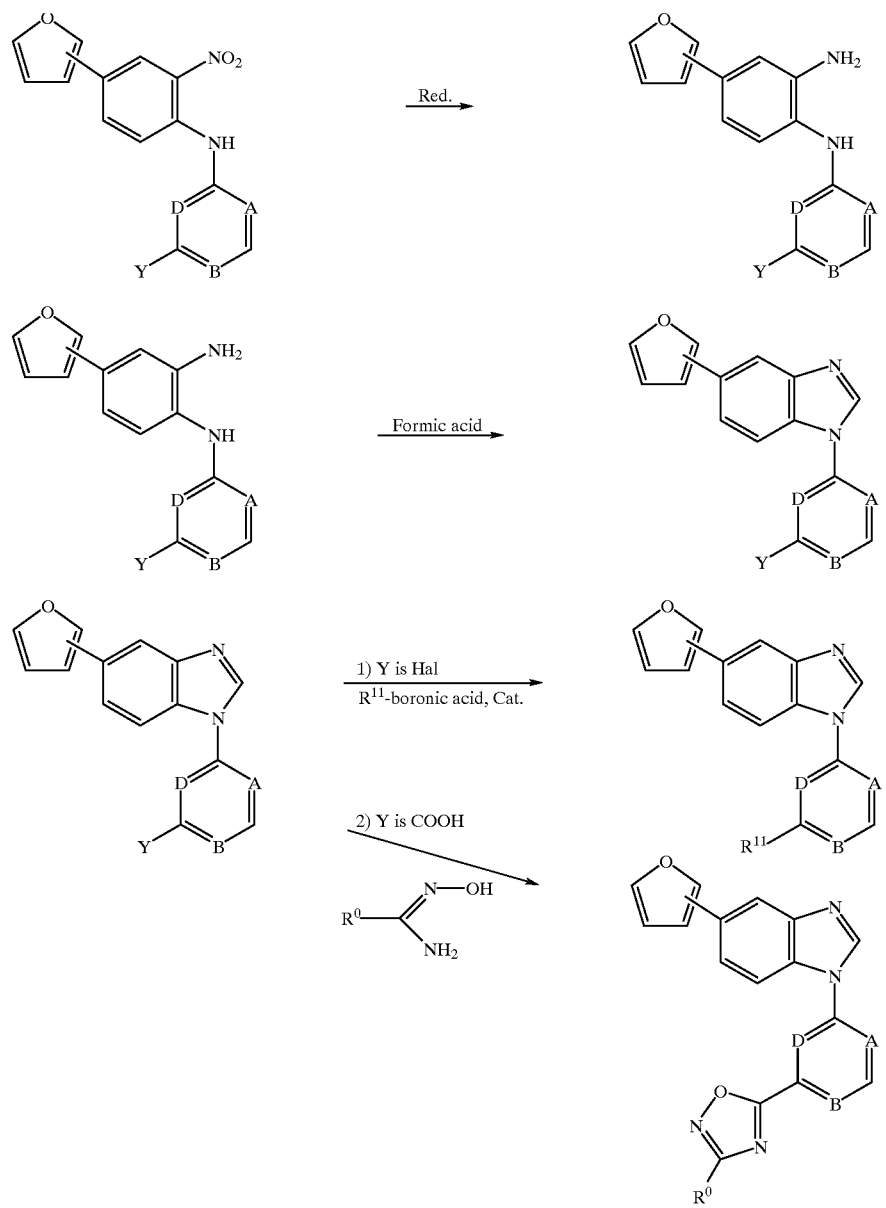
d)
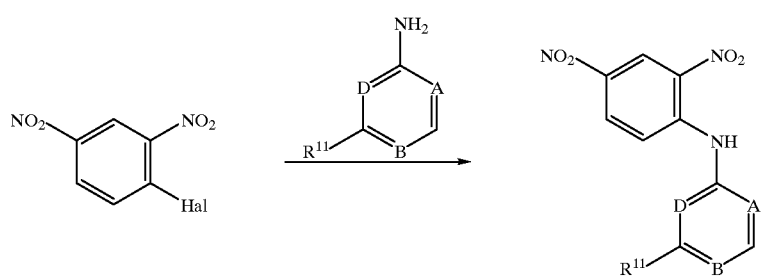

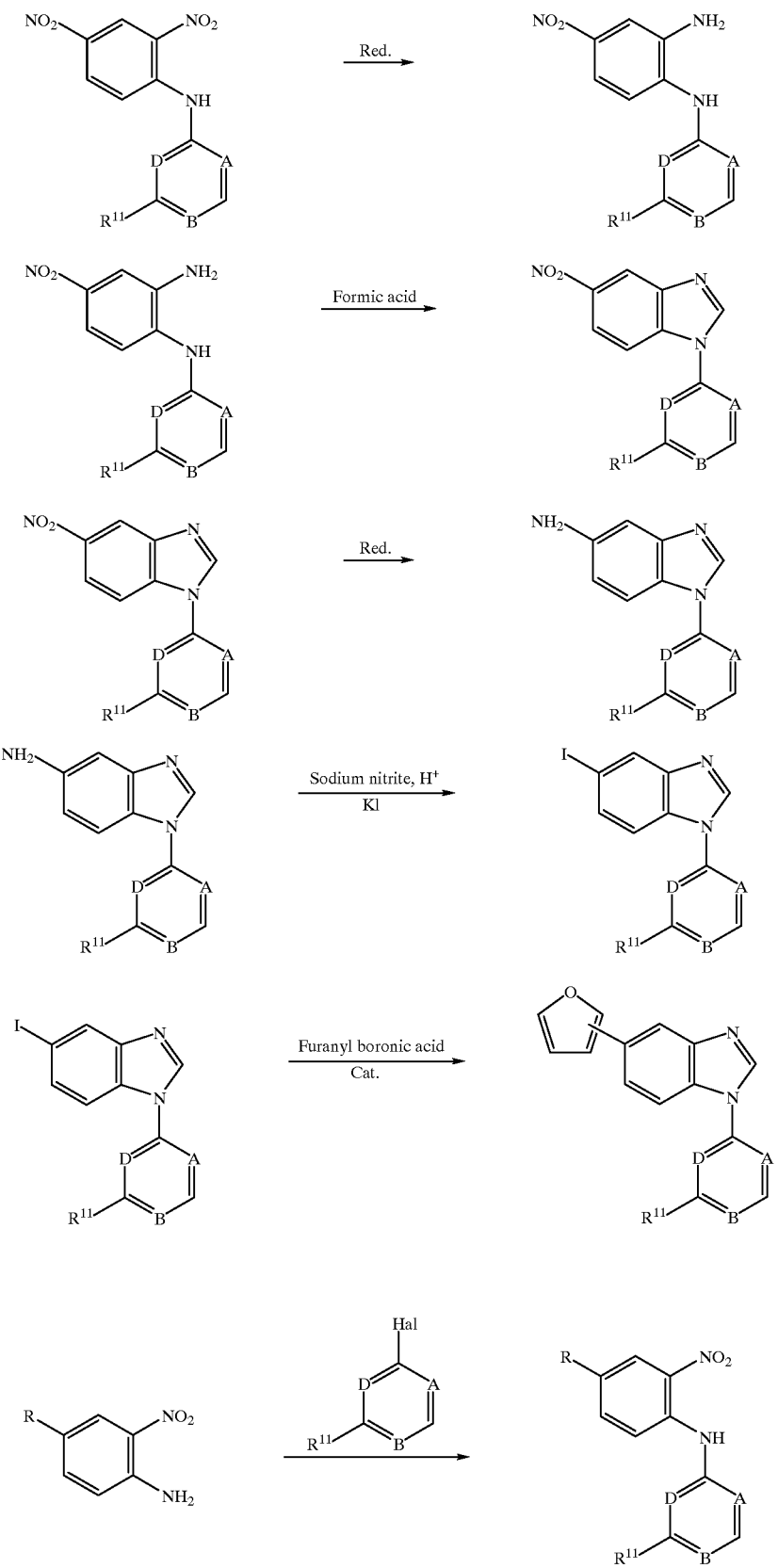
e)

-continued
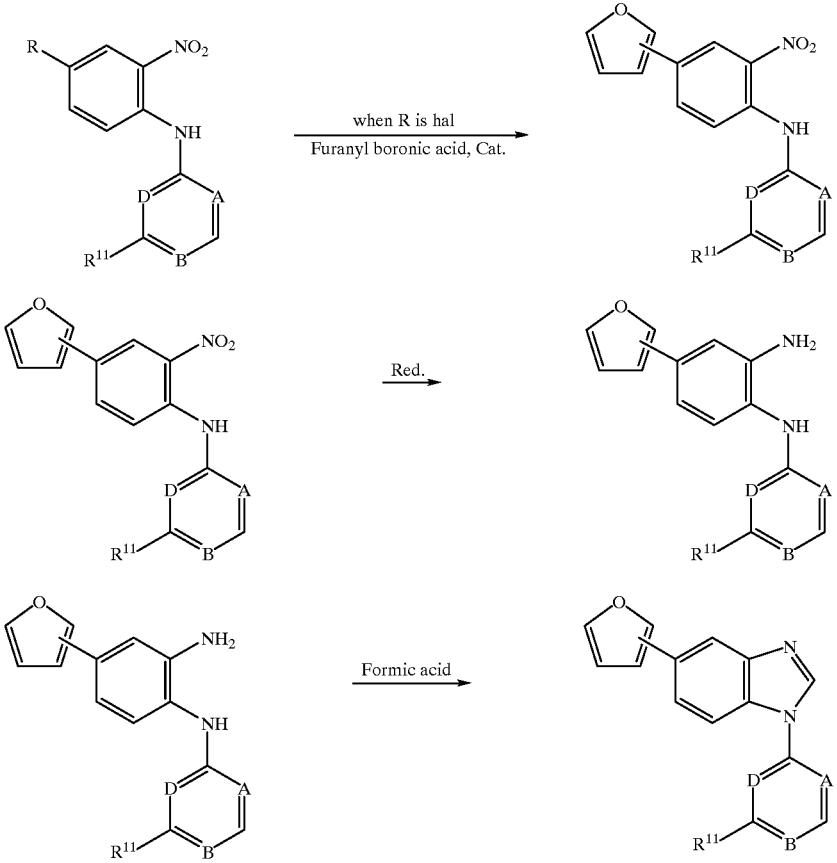
and f)
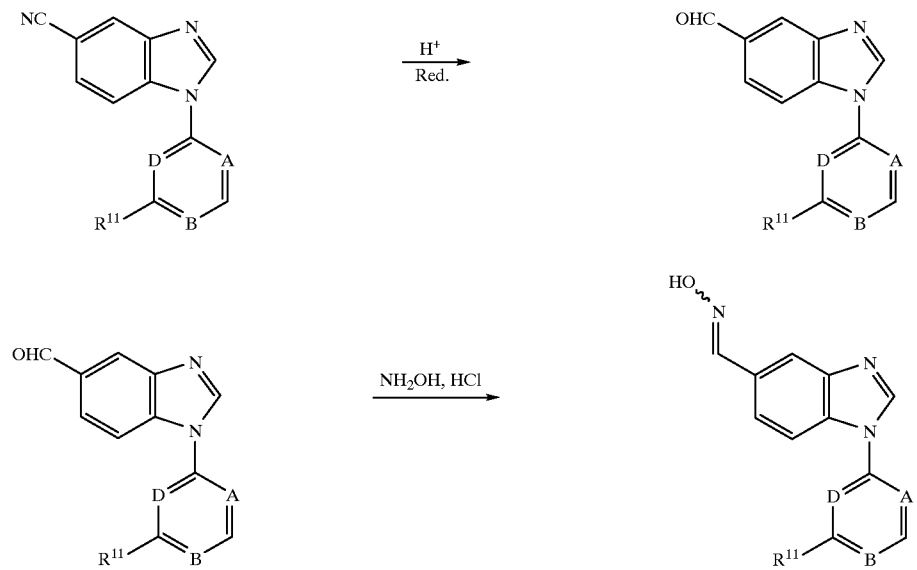

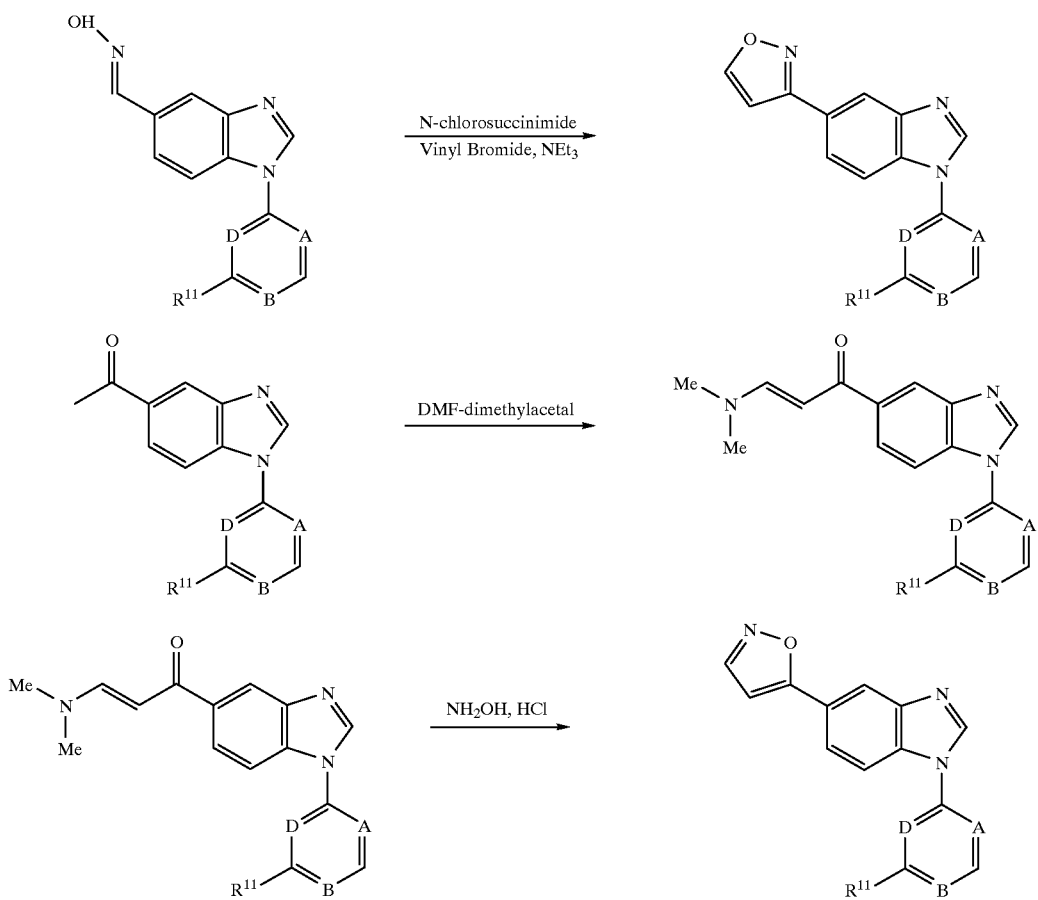
wherein x is hydrogen or acetyl; A, B, D and R[11] are as defined above; Cat is tetrakis(triphenylphosphine)palladium (0); Hal is halogen; Y is halogen or carboxy; R⁰ is alkyl, phenyl or heteroaryl, and R is halogen or furanyl.
14. The method of claim 13 further comprising resolving racemic forms of the compounds into optical isomers.
* * * * *